US006218389B1

(12) United States Patent
Almstead et al.

(10) Patent No.: US 6,218,389 B1
(45) Date of Patent: Apr. 17, 2001

(54) ACYCLIC METALLOPROTEASE INHIBITORS

(75) Inventors: Neil Gregory Almstead, Loveland; Roger Gunnard Bookland, Cincinatti; Yetunde Olabisi Taiwo, West Chester; Rimma Sandler Bradley; Rodney Dean Bush, both of Fairfield; Biswanath De, Cincinatti; Michael George Natchus, Glendale; Stanislaw Pikul, Mason, all of OH (US)

(73) Assignee: The Procter & Gamble Co., Cincinnati, OH (US)

(*) Notice: Subject to any disclaimer, the term of this patent is extended or adjusted under 35 U.S.C. 154(b) by 0 days.

(21) Appl. No.: 09/127,678

(22) Filed: Jul. 31, 1998

Related U.S. Application Data

(60) Provisional application No. 60/054,348, filed on Jul. 31, 1997.

(51) Int. Cl.[7] .................. A61K 31/535; A61K 31/415; C07C 239/00; C07C 211/06; C07D 241/04

(52) U.S. Cl. ............... 514/237.5; 514/255; 514/331; 514/370; 514/389; 514/417; 514/617; 514/618; 514/620; 514/824; 514/825; 514/826; 514/887; 514/902; 514/903; 544/386; 544/388; 546/225; 546/232; 546/233; 548/182; 548/184; 548/317.1; 548/473; 564/48; 564/50; 564/154; 564/163; 564/164; 564/191; 564/197

(58) Field of Search ........................ 564/50, 48, 154, 564/163, 164, 191, 199; 544/386, 388; 546/225, 232, 233; 548/182, 184, 317.1, 473; 514/824, 825, 820, 887, 902, 903, 237.5, 255, 331, 379, 384, 417, 617, 618, 620

(56) References Cited

U.S. PATENT DOCUMENTS

| | | | |
|---|---|---|---|
| 4,918,105 | 4/1990 | Cartwright et al. | 514/575 |
| 4,954,158 | 8/1980 | Stammor | 518/152 |
| 4,996,358 | 2/1991 | Handa et al. | 562/621 |
| 5,183,900 | 2/1993 | Galardy et al. | 548/495 |
| 5,189,178 | 2/1993 | Galardy et al. | 548/495 |
| 5,300,674 | 4/1994 | Crimmin et al. | 560/42 |
| 5,310,763 | 5/1994 | Campion et al. | 514/575 |
| 5,380,941 * | 1/1995 | Siegel et al. | 564/48 |
| 5,442,110 | 8/1995 | Isomura et al. | 562/261 |
| 5,455,258 | 10/1995 | MacPherson et al. | 514/357 |
| 5,534,541 | 7/1996 | Drauz et al. | 514/448 |

FOREIGN PATENT DOCUMENTS

| | | |
|---|---|---|
| 4127842 | 2/1993 | (DE) . |
| 0 231 081 | 8/1987 | (EP) . |
| 0 498 665 | 8/1992 | (EP) . |
| 0 575 844 | 12/1993 | (EP) . |
| 0 606 046 | 7/1994 | (EP) . |
| 0 757 984 | 2/1997 | (EP) . |
| 0 709 490 | 4/1997 | (EP) . |
| 0 915 086 | 5/1999 | (EP) . |
| 0 950 656 | 10/1999 | (EP) . |
| 2 268 934 | 1/1994 | (GB) . |
| WO 88/02627 | 4/1988 | (WO) . |
| WO 91/02716 | 3/1991 | (WO) . |
| WO 92/17460 | 10/1992 | (WO) . |
| WO 93/00082 | 1/1993 | (WO) . |
| WO 93/20047 | 10/1993 | (WO) . |
| WO 93/21942 | 11/1993 | (WO) . |
| WO 94/10990 | 5/1994 | (WO) . |
| WO 95/35275 | 12/1995 | (WO) . |
| WO 95/35276 | 12/1995 | (WO) . |
| WO 96/33172 | 10/1996 | (WO) . |
| WO 97/05865 | 2/1997 | (WO) . |
| WO 97/20824 | 6/1997 | (WO) . |
| WO 97/24349 | 7/1997 | (WO) . |
| WO 97/25315 | 7/1997 | (WO) . |
| WO 97/32846 | 9/1997 | (WO) . |
| WO 97/49674 | 12/1997 | (WO) . |
| WO 98/07742 | 2/1998 | (WO) . |
| WO 98/08814 | 3/1998 | (WO) . |

(List continued on next page.)

OTHER PUBLICATIONS

Kahl, J.U. et al., "Synthesis of Two Naturally Occuring Diastereomeric Dihydroxyprolines: 2,3–trans–3,4–Dihydroxy–I–proline and 2,3–cis–3,4–trans–3,4–Dihydroxy–I–proline", *Liebigs Ann. Chem.*, 1981, pp. 1445–1450.

Hudson, C.B. et al., "On the Synthesis of 3,4–Dihydroxyprolines I. Cis–Glyolation of 3,4–Dehydroproline Derivatives", *Aust. J. Chem.*, vol. 21, 1968, pp. 769–782.

Andreatta, R.H., "Synthesis of Cis and Trans Isomers of 4–Chioro–$_L$ Proline, 4–Bromo–$_L$Proline and 4–Amino–$_L$ Proline", *Aust. J. Chem.*, vol. 20, 1967, pp. 1493–1509.

(List continued on next page.)

*Primary Examiner*—John Kight
*Assistant Examiner*—Raymond Covington
(74) *Attorney, Agent, or Firm*—James C. Kellerman; Carl J. Roof

(57) ABSTRACT

The invention provides compounds of formula (I)

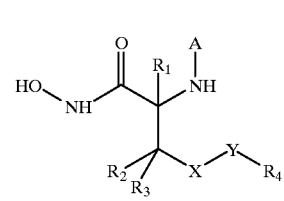

as described in the claims, or an optical isomer, diastereomer or enantiomer thereof, or a pharmaceutically-acceptable salt, or biohydrolyzable amide, ester, or imide thereof are useful as inhibitors of metalloproteases.

Also disclosed are pharmaceutical compositions and methods of treating diseases, disorders and conditions characterized by metalloprotease activity using these compounds or the pharmaceutical compositions containing them.

29 Claims, No Drawings

FOREIGN PATENT DOCUMENTS

WO 98/08815   3/1998   (WO) .
WO 98/08822   3/1998   (WO) .
WO 98/08823   3/1998   (WO) .
WO 98/08825   3/1998   (WO) .
WO 98/08827   3/1998   (WO) .
WO 98/08850   3/1998   (WO) .
WO 98/08853   3/1998   (WO) .
WO 98/17645   4/1998   (WO) .
WO 98/31664   7/1998   (WO) .
WO 98/33768   8/1998   (WO) .
WO 98/42659   10/1998  (WO) .
WO 98/43963   10/1998  (WO) .

OTHER PUBLICATIONS

Heintzelman, G.R. et al., "Imino Diels–Alder–Based Construction of a Piperidine A–Ring Unit for Total Synthesis of the Marine Hepatotoxin Cylindrospermopsin", *Chemical Abstracts*, vol. 125, No. 5, 1996, Abstract No. 58826.

Edwards, M.L., et al., "Synthesis and Enzymic Resolution of a Carbocyclic Analog of Ribofuranosylamine", *Chemical Abstracts*, vol. 125, No. 1,1996, Abstract No. 11281.

Herdeis, C., et al., "Amino Acids, XII. (+)–Pipecolic Acid Derivatives. Part 2, An Expedient Synthetic Entry to Substituted Pipecolic Acids", *Chemical Abstracts*, vol. 117, No. 17, 1992, Abstract No. 17 1989. Natelson, S. "Preparation of D–, DL–, and L–Homoserine Lactone from Methionine", *Microchemical Journal*, vol. 40, 1989, pp. 226–232.

Hansel, J.G., et al., "Oxazoline Formation via a Palladium–catalyzed Cyclization: A Direct Stereoselective Approach to cis–5–amino–2–cyclopenten–1–ol Derivatives", *Tetrahedron Letters*, vol. 30, No. 17, 1995, pp. 2913–2916.

Sarrao, M.P., "BMP 1 and the Astacin Family of Metalloproteinases: a Potential Link Between the Extracellular Matrix, Growth Factors, and Pattern Formation", *BioEssays*, vol. 18, No. 6, 1996 (Abstract attached).

Yoneda, N., et al., "Reaction of L–alpha–tosylamido–beta–proplolactone I. Synthesis Reactions with Amines and Derivation to l–serine", *Yakugaku Zasshi*, vol. 89, No. 1, 1969 (Abstract attached).

Johnson, W.H., et al., "Collagenase Inhibitors: Their Design and Potential Therapeutic Use", *J. Enyzme Inhibition*, vol. 2, 1987, pp. 1–22.

Schwartz, M.A., et al., "8 Synthesis Inhibitors of Bacterial and Mammalian Interstitial Collagenases", *Progress in Medicinal Chemistry*, vol. 29, 1992, pp. 271–334.

Singh, J., et al., "Relationship Between Structure and Bioavailability in a Series of Hydroxamate Based Metalloprotease Inhibitors", *Bioorganic & Medicinal Chemistry Letters*, vol. 5, No. 4, 1995, pp. 337–342.

Tomozuk, B.E., et al., "Hydroxomate Inhibitors of the matrix Metallo–Proteinaseses ($MMP_3$) Containing Novel $P_{1^1}$ Heteroatom Based Modifications", *Bioorganic & Medicianl Chemistry Letters*, vol. 5, No. 4, 1995, pp. 343–348.

Chapman, K.T., et al., "Inhibition of Matrix Metalloproteinases by N–Carboxyalkyl Peptides", *J. Med. Chem.*, vol. 36, 1993, pp. 429–4301.

Turbanti, L., et al., "1,2–Cyclomethylenecarboxylic Monoamide Hydroxamic Derivatives, A Novel Class of Non–Amino Angiotensin Converting Enzyme Inhibitors"*J. Med. Chem.*, vol. 36. 1993. pp. 699–707.

Chemical Abstract vol. 131 No. 29193, Walter et al, "Hydroxaniato Inhibitors of *Anomoas hydrophila* HE 036 Metallic–B–Laitamose"(1994) .*

* cited by examiner

ACYCLIC METALLOPROTEASE INHIBITORS

CROSS REFERENCE

This application claims priority under Title 35, United States Code 119(e) from Provisional Application Ser. No. 60/054,348, filed Jul. 31, 1997.

TECHNICAL FIELD

This invention is directed to compounds which are useful in treating diseases, disorders and conditions associated with unwanted metalloprotease activity.

BACKGROUND

A number of structurally related metalloproteases [MPs] effect the breakdown of structural proteins. These metalloproteases often act on the intercellular matrix, and thus are involved in tissue breakdown and remodeling. Such proteins are referred to as metalloproteases or MPs. There are several different families of MPs, classified by sequence homology. Several families of known MPs, as well as examples thereof, are disclosed in the art.

These MPs include Matrix-Metallo Proteases [MMPs], zinc metalloproteases, many of the membrane bound metalloproteases, TNF converting enzymes, angiotensin-converting enzymes (ACEs), disintegrins, including ADAMs (See Wolfsberg et al, 131 *J. Cell Bio.* 275–78 October, 1995), and the enkephalinases. Examples of MPs include human skin fibroblast collagenase, human skin fibroblast gelatinase, human sputum collagenase, aggrecanse and gelatinase, and human stromelysin. Collagenase, stromelysin, aggrecanase and related enzymes are thought to be important in mediating the symptomatology of a number of diseases.

Potential therapeutic indications of MP inhibitors have been discussed in the literature. See for example, U.S. Pat. No. 5,506,242 (Ciba Geigy Corp.); U.S. Pat. No. 5.403,952 (Merck & Co.); PCT published application WO 96/06074 (British Bio Tech Ltd); PCT Publication WO 96/00214 (Ciba Geigy); WO 95/35275 (British Bio Tech Ltd); WO 95/35276 (British Bio Tech Ltd); WO 95/33731 (Hoffman-LaRoche); WO 95/33709 (Hoffman-LaRoche); WO 95/32944 (British Bio Tech Ltd); WO 95/26989 (Merck); WO 9529892 (DuPont Merck); WO 95/24921 (Inst. Opthamology); WO 95/23790 (SmithKline Beecham); WO 95/22966 (Sanofi Winthrop); WO 95/19965 (Glycomed); WO 95 19956 (British Bio Tech Ltd); WO 95/19957 (British Bio Tech Ltd); WO 95/19961 (British Bio Tech Ltd) WO 95/13289 (Chiroscience Ltd.); WO 95/12603 (Syntex); WO 95/09633 (Florida State Univ); WO 95/09620 (Florida State Univ.); WO 95/04033 (Celltech); WO 94/25434 (Celltech); WO 94/25435 (Celltech); WO 93/14112 (Merck); WO 94/0019 (Glaxo); WO 93/21942 (British Bio Tech Ltd); WO 92/22523 (Res. Corp.

Tech. Inc.); WO 94/10990 (British Bio Tech Ltd); WO 93/09090 (Yamanouchi); and British patents GB 2282598 (Merck) and GB 2268934 (British Bio Tech Ltd); Published European Patent Applications EP 95/684240 (Hoffman LaRoche); EP 574758 (Hoffman LaRoche); EP 575844 (Hoffman LaRoche); Published Japanese applications; JP 08053403 (Fujusowa Pharm.

Co. Ltd.); JP 7304770 (Kanebo Ltd.); and Bird et al *J. Med Chem vol.* 37, pp. 158–69 (1994).

Examples of potential therapeutic uses of MP inhibitors include rheumatoid arthritis (Mullins, D. E., et al., *Biochem. Biophys. Acta.* (1983) 695:117–214); osteoarthritis (Henderson, B., et al., *Drugs of the Future* (1990) 15:495–508); the metastasis of tumor cells (ibid, Broadhurst, M. J., et al., European Patent Application 276,436 (published 1987), Reich, R., et al., 48 *Cancer Res.* 3307–3312 (1988); and various ulcerations or ulcerative conditions of tissue. For example, ulcerative conditions can result in the cornea as the result of alkali burns or as a result of infection by *Pseudomonas aeruginosa*, Acanthamoeba, Herpes simplex and vaccinia viruses.

Other examples of conditions characterized by undesired metalloprotease activity include periodontal disease, epidermolysis bullosa, fever, inflammation and scleritis (Cf. DeCicco et al, WO 95 29892 published Nov. 9, 1995).

In view of the involvement of such metalloproteases in a number of disease conditions, attempts have been made to prepare inhibitors to these enzymes. A number of such inhibitors are disclosed in the literature. Examples include U.S. Pat. No. 5,183,900, issued Feb. 2, 1993 to Galardy; U.S. Pat. No. 4,996,358, issued Feb. 26, 1991 to Handa, et al.; U.S. Pat. No. 4,771,038, issued Sep. 13, 1988 to Wolanin, et al.; U.S. Pat. No. 4,743,587, issued May 10, 1988 to Dickens, et al., European Patent Publication Number 575,844, published Dec. 29, 1993 by Broadhurst, et al.; International Patent Publication No. WO 93/09090, published May 13, 1993 by Isomura, et al.; World Patent Publication 92/17460, published Oct. 15, 1992 by Markwell et al.; and European Patent Publication Number 498,665, published Aug. 12, 1992 by Beckett, et al.

Metalloprotease inhibitors are useful in treating diseases caused, at least in part, by breakdown of structural proteins. Though a variety of inhibitors have been prepared, there is a continuing need for potent matrix metalloprotease inhibitors useful in treating such diseases. Applicants have found that, surprisingly, the lactam-containing acyclic compounds of the present invention are potent metalloprotease inhibitors.

OBJECTS OF THE INVENTION

Thus it is an object of the present invention to provide compounds useful for the treatment of conditions and diseases which are characterized by unwanted MP activity.

It is also an object of the invention to provide potent inhibitors of metalloproteases.

It is a further object of the invention to provide pharmaceutical compositions comprising such inhibitors.

It is also an object of the invention to provide a method of treatment for metalloprotease related maladies.

SUMMARY OF THE INVENTION

The invention provides compounds which are useful as inhibitors of metalloproteases, and which are effective in treating conditions characterized by excess activity of these enzymes. In particular, the present invention relates to a compound having a structure according to Formula (I)

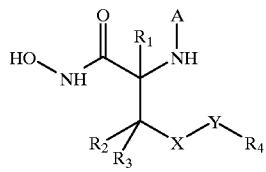

(I)

wherein

A is SO$_2$Ar, COAr, CONHAr, PORAr, where Ar is monocyclic or bicyclic aromatic or a monocyclic or bicyclic heteroaromatic, substituted or unsubstituted;

R$_1$ is alkyl or hydrogen;

R$_2$, R$_3$, and R$_4$ are each independently chosen from hydrogen, alkyl, aryl, heteroaryl, aryl-alkyl, alkoxyalkyl, heterocycle, heterocycle alkyl, and these substituents may be substituted or unsubstituted; rings can be formed by R$_2$ and R$_3$, R$_1$ and R$_2$ or R$_3$ and R$_4$;

X is a bond, a (C$_1$–C$_6$)alkyl, CO, or a heteroatom chosen from O, N, NZ, S, SO, or SO$_2$;

Y is a bond, a (C$_1$–C$_6$)alkyl, CO, CO$_2$, CONH, or a heteroatom chosen from O, N, NZ, S, SO, or SO$_2$; and Z is hydrogen, COR$_4$, COOR$_4$, CONHR$_4$, R$_4$, CSR$_4$, CSNHR$_4$, and SO$_2$R$_4$.

This structure also includes an optical isomer, diastereomer or enantiomer for Formula (I), or a pharmaceutically-acceptable salt, or biohydrolyzable amide, ester, or imide thereof, an optical isomer, diastereomer or enantiomer for Formula (I), or a pharmaceutically-acceptable salt, or biohydrolyzable amide, ester, or imide thereof.

This structure also includes an optical isomer, diastereomer or enantiomer for Formula (I), or a pharmaceutically-acceptable salt, or biohydrolyzable amide, ester, or imide thereof.

These compounds have the ability to inhibit at least one mammalian metalloprotease. Accordingly, in other aspects, the invention is directed to pharmaceutical compositions containing the compounds of Formula (I), and to methods of treating diseases characterized by unwanted metalloprotease activity using these compounds or the pharmaceutical compositions containing them.

Metalloproteases which are active at a particularly undesired location (e.g., an organ or certain types of cells) can be targeted by conjugating the compounds of the invention to a targeting ligand specific for a marker at that location such as an antibody or fragment thereof or a receptor ligand. Conjugation methods are known in the art.

The invention is also directed to various other processes which take advantage of the unique properties of these compounds. Thus, in another aspect, the invention is directed to the compounds of Formula (I) conjugated to solid supports. These conjugates can be used as affinity reagents for the purification of a desired metalloprotease.

In another aspect, the invention is directed to the compounds of Formula (I) conjugated to label. As the compounds of the invention bind to at least one metalloprotease, the label can be used to detect the presence of relatively high levels of metalloprotease, preferably a matrix metalloprotease in vivo or in vitro cell culture.

In addition, the compounds of Formula (I) can be conjugated to carriers which permit the use of these compounds in immunization protocols to prepare antibodies specifically immunoreactive with the compounds of the invention. Typical conjugation methods are known in the art. These antibodies are then useful both in therapy and in monitoring the dosage of the inhibitors.

DETAILED DESCRIPTION

The compounds of the present invention are inhibitors of mammalian metalloproteases, preferably a matrix metalloproteases. Preferably, the compounds are those of Formula (I) or a pharmaceutically-acceptable salt, or biohydrolyzable amide, ester, or imide thereof.

Throughout this disclosure, publications and patents are referred to in an effort to fully describe the state of the art. All references cited herein are hereby incorporated by reference.

Definitions and Usage of Terms

The following is a list of definitions for terms used herein.

"Acyl" or "carbonyl" is described as a radical which could be formed by removal of the hydroxy from a carboxylic acid (i.e., R—C(=O)—). Preferred acyl groups include (for example) acetyl, formyl, and propionyl.

"Acyloxy" is an oxy radical having an acyl substituent (i.e., —O-acyl); for example, —O—C(=O)-alkyl.

"Alkoxyacyl" is an acyl radical (—C(=O)—) having an alkoxy substituent (i.e., —O—R), for example, —C(=O)—O-alkyl. This radical can be referred to as an ester.

"Acylamino" is an amino radical having an acyl substituent (i.e., —N-acyl); for example, —NH—C(=O)-alkyl.

"Alkenyl" is an unsubstituted or substituted hydrocarbon chain radical having 2 to 15 carbon atoms; preferably from 2 to 10 carbon atoms; more preferably from 2 to 8; except where indicated. Alkenyl substituents have at least one olefinic double bond (including, for example, vinyl, allyl and butenyl).

"Alkynyl" is an unsubstituted or substituted hydrocarbon chain radical having 2 to 15 carbon atoms; preferably from 2 to 10 carbon atoms; more preferably from 2 to 8; except where indicated. The chain has at least one carbon-carbon triple bond.

"Alkoxy" is an oxygen radical having a hydrocarbon chain substituent, where the hydrocarbon chain is an alkyl or alkenyl (i.e., —O-alkyl or —O-alkenyl). Preferred alkoxy groups include (for example) methoxy, ethoxy, propoxy and allyloxy.

"Alkoxyalkyl" is an unsubstituted or substituted alkyl moiety substituted with an alkoxy moiety (i.e., -alkyl-O-alkyl). Preferred is where the alkyl has 1 to 6 carbon atoms (more preferably 1 to 3 carbon atoms), and the alkyoxy has 1 to 6 carbon atoms (more preferably 1 to 3 carbon atoms).

"Alkyl" is an unsubstituted or substituted saturated hydrocarbon chain radical having 1 to 15 carbon atoms; preferably from 1 to 10 carbon atoms; more preferably 1 to 4; except where indicated. Preferred alkyl groups include (for example) substituted or unsubstituted methyl, ethyl, propyl, isopropyl, and butyl.

As referred to herein, "spiro cycle" or "spiro cyclic" refers to a cyclic moiety sharing a carbon on another ring. Such cyclic moiety may be carbocyclic or heterocyclic in nature. Preferred heteroatoms included in the backbone of the heterocyclic spirocycle include oxygen, nitrogen and sulfur. The spiro cycles may be unsubstituted or substituted. Preferred substituents include oxo, hydroxy, alkyl, cycloalkyl, arylalkyl, alkoxy, amino, heteroalkyl, aryloxy, fused rings (e.g., benzothiole, cycloalkyl, heterocycloalkyl, benzimidizoles, pyridylthiole, etc., which may also be substituted) and the like. In addition, the heteroatom of the heterocycle may be substituted if valence allows. Preferred spirocyclic ring sizes include 3–7 membered rings.

"Alkylene" refers to an alkyl, alkenyl or alkynyl which is diradical, rather than a radical. "Hetero alkylene" is likewise defined as a (diradical) alkylene having a heteroatom in its chain.

"Alkylamino" is an amino radical having one (secondary amine) or two (tertiary amine) alkyl substituents (i.e., —N-alkyl). For example, methylamino (—NHCH$_3$), dimethylamino (—N(CH$_3$)$_2$), methylethylamino (—N(CH$_3$)CH$_2$CH$_3$).

"Amino acid" includes any naturally occurring amino acids, their d-amine variants include any α-amino carboxylic acid. As such, pipecolic acid, sarcosine and thus, are contemplated.

"Aminoacyl" is acyl radical having an amino substituent (i.e., —C(=O)—N); for example, —C(=O)—NH$_2$. The amino group of the aminoacyl moiety may be unsubstituted (i.e., primary amine) or may be substituted with one (secondary amine) or two (i.e., tertiary amine)alkyl groups.

"Aryl" is an aromatic carbocyclic ring radical. Preferred aryl groups include (for example) phenyl, tolyl, xylyl, cumenyl, naphthyl, biphenyl and fluorenyl. Such groups may be substituted or unsubstituted.

"Arylalkyl" is an alkyl radical substituted with an aryl group. Preferred arylalkyl groups include benzyl, phenylethyl, and phenylpropyl. Such groups may be substituted or unsubstituted. "Arylalkylamino" is an amine radical substituted with an arylalkyl group (e.g., —NH-benzyl). Such groups may be substituted or unsubstituted.

"Arylamino" is an amine radical substituted with an aryl group (i.e., —NH-aryl). Such groups may be substituted or unsubstituted.

"Aryloxy" is an oxygen radical having an aryl substituent (i.e., —O-aryl). Such groups may be substituted or unsubstituted.

"Carbocyclic ring" is an unsubstituted or substituted, saturated, unsaturated or aromatic, hydrocarbon ring radical. Carbocyclic rings are monocyclic or are fused, bridged or spiro polycyclic ring systems. Monocyclic carbocyclic rings generally contain 4 to 9 atoms, preferably 4 to 7 atoms. Polycyclic carbocyclic rings contain 7 to 17 atoms, preferably from 7 to 12 atoms. Preferred polycyclic systems comprise 4-, 5-, 6- or 7-membered rings fused to 5-, 6-, or 7-membered rings.

"Carbocycle-alkyl" is an unsubstituted or substituted alkyl radical substituted with a carbocyclic ring. Unless otherwise specified, the carbocyclic ring is preferably an aryl or cycloalkyl; more preferably an aryl. Preferred carbocycle-alkyl groups include benzyl, phenylethyl and phenylpropyl.

"Carbocycle-heteroalkyl" is an unsubstituted or substituted heteroalkyl radical substituted with a carbocyclic ring. Unless otherwise specified, the carbocyclic ring is preferably an aryl or cycloalkyl; more preferably an aryl. The heteroalkyl is preferably 2-oxa-propyl, 2-oxa-ethyl, 2-thia-propyl, or 2-thia-ethyl.

"Carboxyalkyl" is an unsubstituted or substituted alkyl radical substituted with a carboxy (—C(=O)OH) moiety. For example, —CH$_2$—C(=O)OH.

"Cycloalkyl" is a saturated carbocyclic ring radical. Preferred cycloalkyl groups include (for example) cyclopropyl, cyclobutyl and cyclohexyl.

"Cycloheteroalkyl" is a saturated heterocyclic ring. Preferred cycloheteroalkyl groups include (for example) morpholinyl, piperadinyl, piperazinyl, tetrahydrofuryl and hydantoinyl.

"Fused rings" are rings that are superimposed together such that they share two ring atoms. A given ring may be fused to more than one other ring. Fused rings are contemplated in heteroaryl, aryl and heterocycle radicals or the like.

"Heterocycle-alkyl" is an alkyl radical substituted with a heterocyclic ring. The heterocyclic ring is preferably a heteroaryl or cycloheteroalkyl; more preferably a heteroaryl. Preferred heterocycle alkyl include C$_1$–C$_4$ alkyl having preferred heteroaryl appended to them. More preferred is, for example, pyridyl alkyl, and the like.

"Heterocycle-heteroalkyl" is an unsubstituted or substituted heteroalkyl radical substituted with a heterocyclic ring. The heterocyclic ring is preferably an aryl or cycloheteroalkyl; more preferably an aryl.

"Heteroatom" is a nitrogen, sulfur or oxygen atom. Groups containing one or more heteroatoms may contain different heteroatoms.

"Heteroalkenyl" is an unsubstituted or substituted unsaturated chain radical having 3 to 8 members comprising carbon atoms and one or two heteroatoms. The chain has at least one carbon-carbon double bond.

"Heteroalkyl" is an unsubstituted or substituted saturated chain radical having 2 to 8 members comprising carbon atoms and one or two heteroatoms.

"Heterocyclic ring" is an unsubstituted or substituted, saturated, unsaturated or aromatic ring radical comprised of carbon atoms and one or more heteroatoms in the ring. Heterocyclic rings are monocyclic or are fused, bridged or spiro polycyclic ring systems. Monocyclic heterocyclic rings contain 3 to 9 atoms, preferably 4 to 7 atoms. Polycyclic rings contain 7 to 17 atoms, preferably from 7 to 13 atoms.

"Heteroaryl" is an aromatic heterocyclic ring, either monocyclic or bicyclic radical. Preferred heteroaryl groups include (for example) thienyl, furyl, pyrrolyl, pyridinyl, pyrazinyl, thiazolyl, pyrimidinyl, quinolinyl, and tetrazolyl, benzo thiazolyl, benzofuryl, indolyl and the like. Such groups may be substituted or unsubstituted.

"Halo", "halogen", or "halide" is a chloro, bromo, fluoro or iodo atom radical. Bromo, chloro and fluoro are preferred halides.

Also, as referred to herein, a "lower" hydrocarbon moiety (e.g., "lower" alkyl) is a hydrocarbon chain comprised of 1 to 6, preferably from 1 to 4, carbon atoms.

A "pharmaceutically-acceptable salt" is a cationic salt formed at any acidic (e.g., carboxyl) group, or an anionic salt formed at any basic (e.g., amino) group. Many such salts are known in the art, as described in World Patent Publication 87/05297, Johnston et al., published Sep. 11, 1987 (incorporated by reference herein). Preferred cationic salts include the alkali metal salts (such as sodium and potassium), and alkaline earth metal salts (such as magnesium and calcium) and organic salts. Preferred anionic salts include the halides (such as chloride salts).

"Biohydrolyzable amides" are amides of the compounds of the invention that do not interfere with the inhibitory activity of the compound, or that are readily converted in vivo by a mammal subject to yield an active inhibitor.

A "biohydrolyzable hydroxy imide" is an imide of a Formula (I) compound that does not interfere with the metalloprotease inhibitory activity of these compounds, or that is readily converted in vivo by a mammal subject to yield an active Formula (I) compound. Such hydroxy imides include those that do not interfere with the biological activity of the Formula (I) compounds.

A "biohydrolyzable ester" refers to an ester of a Formula (I) compound that does not interfere with the metalloprotease inhibitory activity of these compounds or that is readily converted by an animal to yield an active Formula (I) compound.

A "solvate" is a complex formed by the combination of a solute (e.g., a metalloprotease inhibitor) and a solvent (e.g., water). See J. Honig et al., *The Van Nostrand Chemist's Dictionary,* p. 650 (1953). Pharmaceutically-acceptable solvents used according to this invention include those that do not interfere with the biological activity of the metalloprotease inhibitor (e.g., water, ethanol, acetic acid, N,N-dimethylformamide and others known or readily determined by the skilled artisan).

"Optical isomer", "stereoisomer", "diastereomer" as referred to herein have the standard art recognized meanings (Cf., *Hawley's Condensed Chemical Dictionary*, 11th Ed.).

The illustration of specific protected forms and other derivatives of the Formula (I) compounds is not intended to be limiting. The application of other useful protecting groups, salt forms, etc. is within the ability of the skilled artisan.

As defined above and as used herein, substituent groups may themselves be substituted. Such substitution may be with one or more substituents. Such substituents include those listed in C. Hansch and A. Leo, *Substituent Constants for Correlation Analysis in Chemistry and Biology* (1979), incorporated by reference herein. Preferred substituents include (for example) alkyl, alkenyl, alkoxy, hydroxy, oxo, nitro, amino, aminoalkyl (e.g., aminomethyl, etc.), cyano, halo, carboxy, alkoxyaceyl (e.g., carboethoxy, etc.), thiol, aryl, cycloalkyl, heteroaryl, heterocycloalkyl (e.g., piperidinyl, morpholinyl, pyrrolidinyl, etc.), imino, thioxo, hydroxyalkyl, aryloxy, arylalkyl, and combinations thereof.

As used herein, "mammalian metalloprotease" means any metal-containing enzyme found in mammalian sources which is capable of catalyzing the breakdown of collagen, gelatin or proteoglycan under suitable assay conditions. Appropriate assay conditions can be found, for example, in U.S. Pat. No. 4,743,587, which references the procedure of Cawston, et al., *Anal. Biochem.* (1979) 99:340–345, use of a synthetic substrate is described by Weingarten, H., et al., *Biochem. Biophy. Res. Comm.* (1984) 139:1184–1187. Any standard method for analyzing the breakdown of these structural proteins can, of course, be used. The metalloprotease enzymes referred to herein are all zinc-containing proteases which are similar in structure to, for example, human stromelysin or skin fibroblast collagenase. The ability of candidate compounds to inhibit metalloprotease activity can, of course, be tested in the assays described above. Isolated metalloprotease enzymes can be used to confirm the inhibiting activity of the invention compounds, or crude extracts which contain the range of enzymes capable of tissue breakdown can be used.

Compounds

Compounds of the invention are described in the Summary of the Invention.

Preferred A is $SO_2Ar$, where Ar is a monocycclic or bicyclic aromatic or a monocycclic or bicyclic heteroaromatic moiety. This moiety can be substituted or unsubstituted, and may be carbocyclic or heterocyclic, preferred heteroatoms include oxygen, sulfur and nitrogen, the most preferred being nitrogen. By nitrogen, it is understood that the valence of nitrogen is preferred, such that if the preferred aromatic moiety is benximidazole, nitrogen includes NH, to preserve valence. Most preferred aromatics include phenyl and pyridy, most preferably phenyl.

Preferred Ar includes substituted Ar, substitution may be of any number of substituents, and at any position on the aromatic moiety. More preferred substituents are alkoxy, aryloxy, aryl, alkyl and halo. Where the Ar moiety is monocyclic, it is preferred that substitution be at the 2 or 4 position relative to the attachment of the Ar to the sulfur, phosphorous, oxygen, nitrogen or carbonyl carbon of the A moiety.

Preferred $R_1$ includes alkyl, hydrogen, more preferably hydrogen.

Preferred $R_2$, $R_3$ and $R_4$ are independently chosen from hydrogen, alkyl, aryl, heteroaryl, aryl-alkyl, heterocycle, heterocycle alkyl, and these substituents may be substituted or unsubstituted X includes a bond, or a heteroatom chosen from O, N, or S. Of course the valonce of nitrogen allows for =N= and —NZ—, and both are contemplated herein. Z includes $COR_4$, $COOR_4$, $CONHR_4$ and $SO_2R_4$.

In addition, rings can be formed by $R_2$ and $R_3$, thus forming a "spirocyclic ring system," and $R_1$ and $R_2$ or $R_3$ and $R_4$ can form rings. Preferably such rings are 5–7 members in size.

Compound Preparation

The hydroxamic compounds of Formula (I) can be prepared using a variety of procedures. General schemes include the following.

The hydroxamic compounds of Formula (I) can be prepared using a variety of procedures. Generally preferred methods of making the compounds include the following:

A. Preparation of the NHA Portion of the Molecule and Elaboration of the Hydroxamic Acid It is preferred that this portion of the synthesis will proceed via differing routes depending upon the desired A substituent. Where A is $SO_2Ar$, COAr, or PORAr, the synthesis proceeds using amide chemistry. However, where A is CONHAr, it is preferred that the amino acid derivative be reacted with the isocyanate ArNCO, as illustrated below. For simplicity, $R_1$ and the $C(R_2,R_3,X$—Y—$R_4)$ moiety is replaced with Q in this scheme:

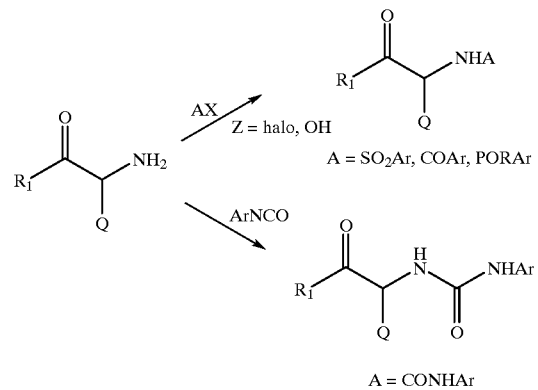

R' is alkyl, alkoxy, hydrogen or any other moitel that can later be elaborated to an acyl halide or the like, amenable to hydroxamic acid synthesis.

The hydroxamic acid moiety is then prepared by standard methods, preferably by preparation of an acyl halide and treatment with hydroxylamine.

B. Elaboration of the "Q Moiety" $[C(R_2,R_3,X$—Y—$R_4)]$

Q $[C(R_2,R_3,X$—Y—$R_4)]$ may be added via a strong base, using for example metal hydrides, in conjunction with carbonyl compound, at an acidic carbon, which would be present alpha to the carbonyl. Of course the skilled artisan would recognize that any free amines on an amino acid would require masking for reasonable yields, as illustrated below. For simplicity, $R_1$ is illustrated as H, and A is other than CONHAr. The skilled artisan will be able to make molecules with differing substitution based on this illustrative scheme:

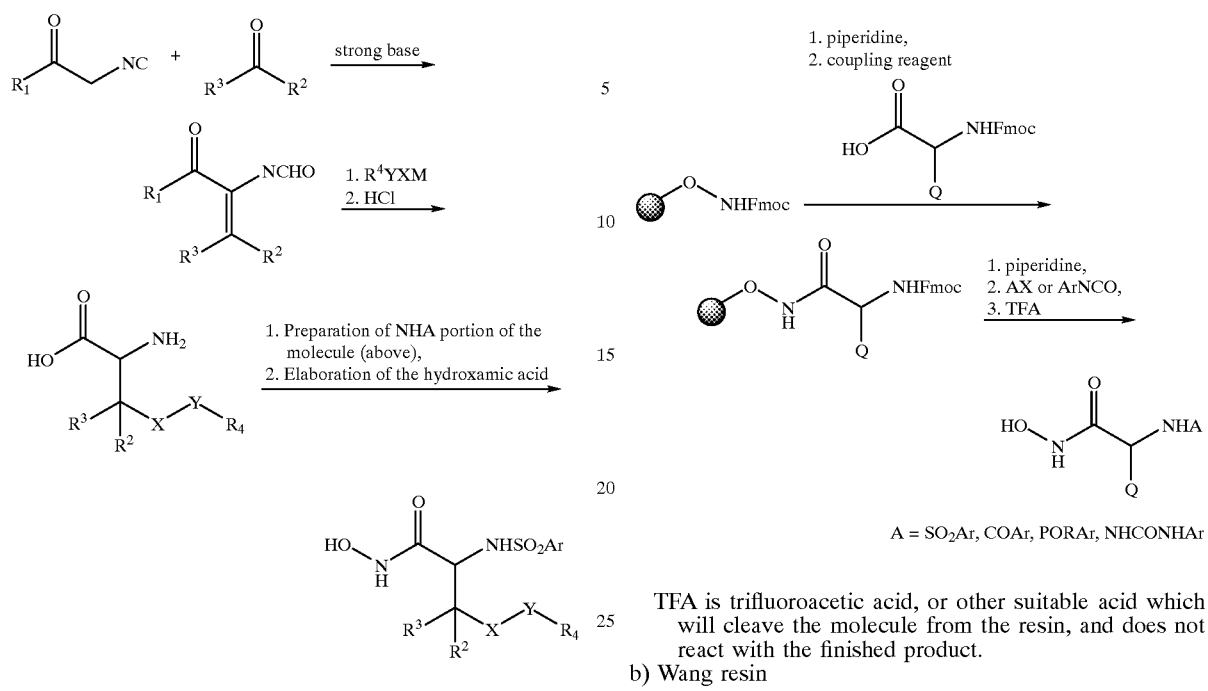

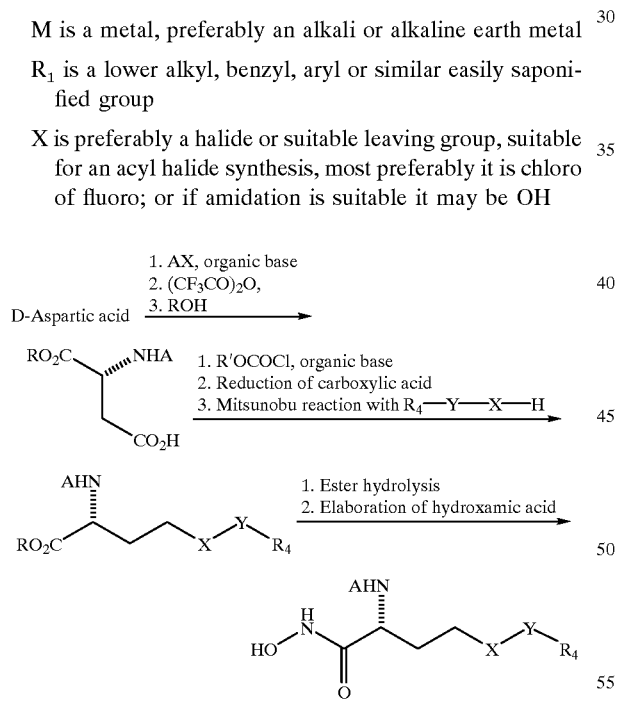

M is a metal, preferably an alkali or alkaline earth metal $R_1$ is a lower alkyl, benzyl, aryl or similar easily saponified group X is preferably a halide or suitable leaving group, suitable for an acyl halide synthesis, most preferably it is chloro of fluoro; or if amidation is suitable it may be OH The compounds of this invention are also amenable to support based synthesis, such as on a column, or in a combinatorial synthesis. Supports for such synthetic methods are new commercially available and methods for using them are generally known. Organic bases are used in synthesis, typically these are nitrogenous bases, and prefered bases include piperidine, triethylamine (TEA), diisopropylamine (DIPEA), and the like. For illustration, two common materials and associated general procedures are described:

a) Chlorotrityl polystyrene resin

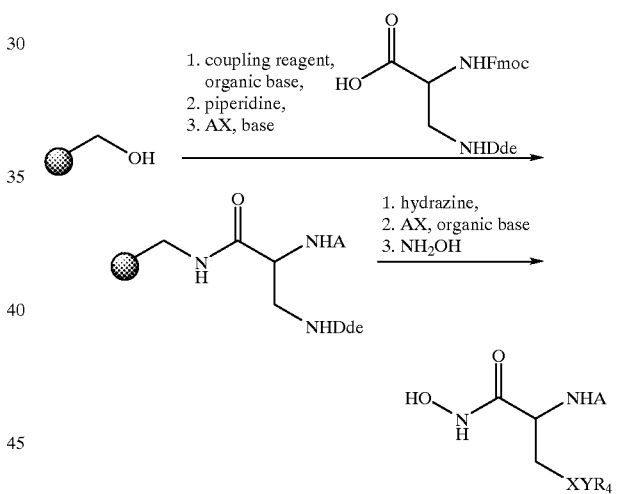

A = $SO_2Ar$, COAr, PORAr, NHCONHAr

TFA is trifluoroacetic acid, or other suitable acid which will cleave the molecule from the resin, and does not react with the finished product.

b) Wang resin

The compounds of Formula (I) are easily prepared from amino acids, amino acid derivatives and the like. Preferably alpha amino is reacted with a compound having halo or a suitable leaving group. Of course, where the amino acid is unavailable the functionality on the reactants may be reversed, i.e., a alpha carbonyl leaving group may be reacted with an amino group. Preferably, a primary amino compound, under basic conditions, displaces the halide or leaving group.

Amino acids, include not only the 20 commonly occurring amino acids and their derivatives (e.g., sarcosine, hydroxy proline, 2-amino butyric acid, pipicolic acid and the like) and any such d-amino acids, but also any alpha amino acid. Many are known or commercially available, such as, from Sigma (St. Louis, Mo.) or Aldrich (Milwaukee, Wis.). For those amino acids that are not available, amino acid variants can be made by any of several methods known in the art.

Using the examples below and the preceeding discussion the skilled artisan can generate a variety of compounds in a similar fashion, using the guidance of the scheme above. These steps may be varied to increase yield of desired product. The skilled artisan will also recognize the judicious choice of reactants, solvents, and temperatures is an important component in successful synthesis. While the determination of optimal conditions, etc. is routine, it will be understood that to make a variety of compounds can be generated in a similar fashion, using the guidance of the scheme above.

The starting materials used in preparing the compounds of the invention are known, made by known methods, or are commercially available as a starting material.

It is recognized that the skilled artisan in the art of organic chemistry can readily carry out standard manipulations of organic compounds without further direction; that is, it is well within the scope and practice of the skilled artisan to carry out such manipulations. These include, but are not limited to, reduction of carbonyl compounds to their corresponding alcohols, oxidations of hydroxyls and the like, acylations, aromatic substitutions, both electrophilic and nucleophilic, etherifications, esterification and saponification and the like. Examples of these manipulations are discussed in standard texts such as March, *Advanced Organic Chemistry* (Wiley), Carey and Sundberg, *Advanced Organic Chemistry* (Vol. 2).

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene, *Protecting Groups in Organic Synthesis*. Of course, amino acids used as starting materials with reactive side chains are preferably blocked to prevent undesired side reactions.

The compounds of the invention may have one or more chiral centers. As a result, one may selectively prepare one optical isomer, including diastereomer and enantiomer, over another, for example by chiral starting materials, catalysts or solvents, or may prepare both stereoisomers or both optical isomers, including diastereomers and enantiomers at once (a racemic mixture). Since the compounds of the invention may exist as racemic mixtures, mixtures of optical isomers, including diastereomers and enantiomers, or stereoisomers may be separated using known methods, such as chiral salts, chiral chromatography and the like.

In addition, it is recognized that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantiomers, or stereoisomers substantially free of the other are disclosed and claimed as well.

Methods of Use

Metalloproteases (MPs) found in the body operate, in part, by breaking down the extracellular matrix, which comprises extracellular proteins and glycoproteins. These proteins and glycoproteins play an important role in maintaining the size, shape, structure and stability of tissue in the body. Inhibitors of metalloproteases are useful in treating diseases caused, at least in part, by breakdown of such proteins. It is known that MPs are intimately involved in tissue remodeling. As a result of this activity they have been said to be active in many disorders involving either the:

breakdown of tissues; including degenerative diseases, such as arthritis, multiple sclerosis and the like; metastasis or mobility of tissues in the body:

the remodeling of tissues, including fibrotic disease, scarring, benign hyperplasia, and the like.

The compounds of the present invention treat disorders, diseases and/or unwanted conditions which are characterized by unwanted or elevated activity by that class of proteases. For example the compounds can be used to inhibit proteases which destroy structural proteins (i.e. the proteins that maintain tissue stability and structure);

interfere in inter/intracellular signaling, including those implicated in cytokine up-regulation, and/or cytokine processing and/or inflammation, tissue degradation and other maladies [Mohler K M, et al, Nature 370 (1994) 218–220, Gearing A J H, et al, Nature 370 (1994) 555–557 McGeehan G M, et al, Nature 370 (1994) 558–561], and/or facilitate processes which are undesired in the subject being treated, for example, the processes of sperm maturation, egg fertilization and the like.

As used herein, a "MP related disorder" or "a MP related disease" is one that involves unwanted or elevated MP activity in the biological manifestation of the disease or disorder; in the biological cascade leading to the disorder; or as a symptom of the disorder. This "involvement" of the MP includes;

The unwanted or elevated MP activity as a "cause" of the disorder or biological manifestation, whether the activity was elevated genetically, by infection, by autoimmunity, trauma, biomechanical causes, lifestyle [e.g. obesity] or by some other cause;

The MP as part of the observable manifestation of the disease or disorder. That is, the disease or disorder is measurable in terms of the increased MP activity, or from a clinical standpoint, unwanted or elevated MP levels indicate the disease. MPs need not be the "hallmark" of the disease or disorder;

The unwanted or elevated MP activity is part of the biochemical or cellular cascade that results or relates to the disease or disorder. In this respect, inhibition of the MP activity interrupts the cascade, and thus controls the disease.

Advantageously, many MPs are not distributed evenly throughout the body. Thus the distribution of MPs expressed in various tissues are often specific to those tissues. For example, the distribution of metalloproteases implicated in the breakdown of tissues in the joints, is not the same as the distribution of metalloproteases found in other tissues. Thus, though not essential for activity or efficacy, certain disorders preferably are treated with compounds that act on specific MPs found in the affected tissues or regions of the body. For example, a compound which displays a higher degree of affinity and inhibition for a MP found in the joints (e.g. chondrocytes) would be preferred for treatment of disease found there than other compounds which are less specific.

In addition, certain inhibitors are more bioavailable to certain tissues than others, and this judicious choice of inhibitor, with the selectivity described above provides for specific treatment of the disorder, disease or unwanted condition. For example, compounds of this invention vary in their ability to penetrate into the central nervous system. Thus compounds may be selected to produce effects mediated through MPs found specifically outside the central nervous system.

Determination of the specificity of a MP inhibitor of a certain MP is within the skill of the artisan in that field. Appropriate assay conditions can be found in the literature. Specifically assays are known for stromelysin and collagenase. For example, U.S. Pat. No. 4,743,587 references the procedure of Cawston, et al., *Anal Biochem* (1979) 99:340–345. The use of a synthetic substrate in an assay is described by Weingarten, H., et al., *Biochem Biophy Res Comm* (1984) 139:1184–1187. Any standard method for analyzing the breakdown of structural proteins by MPs can, of course, be used. The ability of compounds of the invention to inhibit metalloprotease activity can, of course, be tested in the assays found in the literature, or variations thereof. Isolated metalloprotease enzymes can be used to confirm the inhibiting activity of the invention compounds, or crude extracts which contain the range of enzymes capable of tissue breakdown can be used.

As a result of the MP inhibitory effect of the compounds of the invention, the compounds of the invention are also useful in treating the following disorders by virtue of their metalloprotease activity.

The compounds of this invention are also useful for the prophylactic or acute treatment. They are administered in any way the skilled artisan in the fields of medicine or pharmacology would desire. It is immediately apparent to the skilled artisan that preferred routes of administration will depend upon the disease state being treated, and the dosage form chosen. Preferred routes for systemic administration include administration perorally or parenterally.

However, the skilled artisan will readily appreciate the advantage of administering the MP inhibitor directly to the affected area for many disorders. For example, it may be advantageous to administer MP inhibitors directly to the area of the disease or condition as in area affected by surgical trauma (e. g., angioplasty), area affected by scarring or burn (e.g., topical to the skin).

Because the remodeling of bone involves MPs, the compounds of the invention are useful in preventing prosthesis loosening. It is known in the art that over time prostheses loosen, become painful, and may result in further bone injury, thus demanding replacement. The need for replacement of such prostheses includes those such as in, joint replacements (for example hip, knee and shoulder replacements), dental prosthesis, including dentures, bridges and prosthesis secured to the maxilla and/or mandible.

MPs are also active in remodeling of the cardiovascular system (for example, in congestive heart failure). It has been suggested that one of the reasons angioplasty has a higher than expected long term failure rate (reclosure over time) is that MP activity is not desired or is elevated in response to what may be recognized by the body as "injury" to the basement membrane of the vessel. Thus regulation of MP activity in indications such as dilated cardiomyopathy, congestive heart failure, atherosclerosis, plaque rupture, reperfusion injury, ischemia, chronic obstructive pulmonary disease, angioplasty restenosis and aortic aneurysm may increase long term success of any other treatment, or may be a treatment in itself.

In skin care, MPs are implicated in the remodeling or "turnover" of skin. As a result, the regulation of MPs improves treatment of skin conditions including but not limited to, wrinkle repair, regulation and prevention and repair of ultraviolet induced skin damage. Such a treatment includes prophylactic treatment or treatment before the physiological manifestations are obvious. For example, the MP may be applied as a pre-exposure treatment to prevent ultraviolet. damage and/or during or after exposure to pre-vent or minimize post-exposure damage. In addition, MPs are implicated in skin disorders and diseases related to abnormal tissues that result from abnormal turnover, which includes metalloprotease activity, such as epidermolysis bullosa, psoriasis, scleroderma and atopic dermatitis. The compounds of the invention are also useful for treating the consequences of "normal" injury to the skin including scarring or "contraction" of tissue, for example, following burns. MP inhibition is also useful in surgical procedures involving the skin for prevention of scarring, and promotion of normal tissue growth including in such applications as limb reattachment and refractory surgery (whether by laser or incision).

In addition, MPs are related to disorders involving irregular remodeling of other tissues, such as bone, for example, in otosclerosis and/or osteoporosis, or for specific organs, such as in liver cirrhosis and fibrotic lung disease. Similarly in diseases such as multiple sclerosis, MPs may be involved in the irregular modeling of blood brain barrier and/or myelin sheaths of nervous tissue. Thus regulating MP activity may be used as a strategy in treating, preventing, and controlling such diseases.

MPs are also thought to be involved in many infections, including cytomegalovirus; [CMV] retinitis; HIV, and the resulting syndrome, AIDS.

MPs may also be involved in extra vascularization where surrounding tissue needs to be broken down to allow new blood vessels such as in angiofibroma and hemangioma.

Since MPs break down the extracellular matrix, it is contemplated that inhibitors of these enzymes can be used as birth control agents, for example in preventing ovulation, in preventing penetration of the sperm into and through the extracellular milieu of the ovum, implantation of the fertilized ovum and in preventing sperm maturation.

In addition they are also contemplated to be useful in preventing or stopping premature labor and delivery.

Since MPs are implicated in the inflammatory response, and in the processing of cytokines the compounds are also useful as anti-inflammatories, for use in disease where inflammation is prevalent including, inflammatory bowel disease, Crohn's disease, ulcerative colitis, pancreatitis, diverticulitis, asthma or related lung disease, rheumatoid arthritis, gout and Reiter's Syndrome.

Where autoimmunity is the cause of the disorder, the immune response often triggers MP and cytokine activity. Regulation of MPs in treating such autoimmune disorders is a useful treatment strategy. Thus MP inhibitors can be used for treating disorders including, lupus erythmatosis, ankylosing spondylitis, and autoimmune keratitis. Sometimes the side effects of autoimmune therapy result in exacerbation of other conditions mediated by MPs, here MP inhibitor therapy is effective as well, for example, in autoimmune-therapy-induced fibrosis.

In addition, other fibrotic diseases lend themselves to this type of therapy, including pulmonary disease, bronchitis, emphysema, cystic fibrosis, acute respiratory distress syndrome (especially the acute phase response).

Where MPs are implicated in the undesired breakdown of tissue by exogenous agents, these can be treated with MP inhibitors. For example, they are effective as rattle snake bite antidote, as anti-vessicants, in treating allergic inflammation, septicemia and shock. In addition, they are useful as antiparasitics (e.g., in malaria) and antiinfectives. For example, they are thought to be useful in treating or preventing viral infection, including infection which would result in herpes, "cold" (e.g., rhinoviral infection), meningitis, hepatitis, HIV infection and AIDS.

MP inhibitors are also thought to be useful in treating Alzheimer's disease, amyotrophic lateral sclerosis (ALS), muscular dystrophy, complications resulting from or arising out of diabetes, especially those involving loss of tissue viability, coagulation, Graft vs. Host disease, leukemia, cachexia, anorexia, proteinuria, and perhaps regulation of hair growth.

For some diseases, conditions or disorders MP inhibition is contemplated to be a preferred method of treatment. Such diseases, conditions or disorders include, arthritis (including osteoarthritis and rheumatoid arthritis), cancer (especially the prevention or arrest of tumor growth and metastasis), ocular disorders (especially corneal ulceration, lack of corneal healing, macular degeneration, and pterygium), and gum disease (especially periodontal disease, and gingivitis)

Compounds preferred for, but not limited to, the treatment of arthritis (including osteoarthritis and rheumatoid arthritis) are those compounds that are selective for the metalloproteases and the disintegrin metalloproteases.

Compounds preferred for, but not limited to, the treatment of cancer (especially the prevention or arrest of tumor growth and metastasis) are those compounds that preferentially inhibit gelatinases or type IV collagenases.

Compounds preferred for, but not limited to, the treatment of ocular disorders (especially corneal ulceration, lack of corneal healing, macular degeneration, and pterygium) are those compounds that broadly inhibit metalloproteases. Preferably these compounds are administered topically, more preferably as a drop or gel.

Compounds preferred for, but not limited to, the treatment of gum disease (especially periodontal disease, and gingivitis) are those compounds that preferentially inhibit collagenases.

Compositions

The compositions of the invention comprise:
(a) a safe and effective amount of a compound of Formula (I); and
(b) a pharmaceutically-acceptable carrier.

As discussed above, numerous diseases are known to be mediated by excess or undesired metalloprotease activity. These include tumor metastasis, osteoarthritis, rheumatoid arthritis, skin inflammation, ulcerations, particularly of the cornea, reaction to infection, periodontitis and the like. Thus, the compounds of the invention are useful in therapy with regard to conditions involving this unwanted activity.

The invention compounds can therefore be formulated into pharmaceutical compositions for use in treatment or prophylaxis of these conditions. Standard pharmaceutical formulation techniques are used, such as those disclosed in *Remington's Pharmaceutical Sciences,* Mack Publishing Company, Easton, Pa., latest edition.

A "safe and effective amount" of a Formula (I) compound is an amount that is effective, to inhibit metalloproteases at the site(s) of activity, in a mammal subject, without undue adverse side effects (such as toxicity, irritation, or allergic response), commensurate with a reasonable benefit/risk ratio when used in the manner of this invention. The specific "safe and effective amount" will, obviously, vary with such factors as the particular condition being treated, the physical condition of the patient, the duration of treatment, the nature of concurrent therapy (if any), the specific dosage form to be used, the carrier employed, the solubility of the Formula (I) compound therein, and the dosage regimen desired for the composition.

In addition to the subject compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to a mammal. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the animal, preferably mammal being treated.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS™; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

If the subject compound is to be injected, the preferred pharmaceutically-acceptable carrier is sterile, physiological saline, with blood-compatible suspending agent, the pH of which has been adjusted to about 7.4.

In particular, pharmaceutically-acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil. Preferably, the pharmaceutically-acceptable carrier, in compositions for parenteral administration, comprises at least about 90% by weight of the total composition.

The compositions of this invention are preferably provided in unit dosage form. As used herein, a "unit dosage form" is a composition of this invention containing an amount of a Formula (I) compound that is suitable for administration to a aminal, preferably mammal subject, in a single dose, according to good medical practice. These compositions preferably contain from about 5 mg (milligrams) to about 1000 mg, more preferably from about 10 mg to about 500 mg, more preferably from about 10 mg to about 300 mg, of a Formula (I) compound.

The compositions of this invention may be in any of a variety of forms, suitable (for example) for oral, rectal, topical, nasal, ocular or parenteral administration. Depending upon the particular route of administration desired, a variety of pharmaceutically-acceptable carriers well-known in the art may be used. These include solid or liquid fillers, diluents, hydrotropes, surface-active agents, and encapsulating substances. Optional pharmaceutically-active materials may be included, which do not substantially interfere with the inhibitory activity of the Formula (I) compound. The amount of carrier employed in conjunction with the Formula (I) compound is sufficient to provide a practical quantity of material for administration per unit dose of the Formula (I) compound. Techniques and compositions for making dosage forms useful in the methods of this invention are described in the following references, all incorporated by reference herein: *Modern Pharmaceutics,* Chapters 9 and 10 (Banker & Rhodes, editors, 1979); Lieberman et al., *Pharmaceutical Dosage Forms: Tablets* (1981); and Ansel, *Introduction to Pharmaceutical Dosage Forms* 2d Edition (1976).

In addition to the subject compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to a aminal, preferably mammal. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the aminal, preferably mammal being treated.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS™; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

If the subject compound is to be injected, the preferred pharmaceutically-acceptable carrier is sterile, physiological saline, with blood-compatible suspending agent, the pH of which has been adjusted to about 7.4.

Various oral dosage forms can be used, including such solid forms as tablets, capsules, granules and bulk powders. These oral forms comprise a safe and effective amount, usually at least about 5%, and preferably from about 25% to about 50%, of the Formula (I) compound. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration are well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of the subject invention, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions of the subject invention may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compositions of this invention can also be administered topically to a subject, e.g., by the direct laying on or spreading of the composition on the epidermal or epithelial tissue of the subject, or transdermally via a "patch". Such compositions include, for example, lotions, creams, solutions, gels and solids. These topical compositions preferably comprise a safe and effective amount, usually at least about 0.1%, and preferably from about 1% to about 5%, of the Formula (I) compound. Suitable carriers for topical administration preferably remain in place on the skin as a continuous film, and resist being removed by perspiration or immersion in water. Generally, the carrier is organic in nature and capable of having dispersed or dissolved therein the Formula (I) compound. The carrier may include pharmaceutically-acceptable emollients, emulsifiers, thickening agents, solvents and the like.

Methods of Administration

This invention also provides methods of treating or preventing disorders associated with excess or undesired metalloprotease activity in an animal, preferably mammal subject, by administering a safe and effective amount of a Formula (I) compound to said subject. As used herein, a "disorder associated with excess or undesired metalloprotease activity" is any disorder characterized by degradation of proteins. The methods of the invention are useful in treating disorders such as (for example) osteoarthritis, periodontitis, corneal ulceration, tumor invasion, and rheumatoid arthritis.

The Formula (I) compounds and compositions of this invention can be administered topically or systemically. Systemic application includes any method of introducing Formula (I) compound into the tissues of the body, e.g., intra-articular (especially in treatment of rheumatoid arthritis), intrathecal, epidural, intramuscular, transdermal, intravenous, intraperitoneal, subcutaneous, sublingual, rectal, and oral administration. The Formula (I) compounds of the present invention are preferably administered orally.

The specific dosage of inhibitor to be administered, as well as the duration of treatment, and whether the treatment is topical or systemic are interdependent. The dosage and treatment regimen will also depend upon such factors as the specific Formula (I) compound used, the treatment indication, the ability of the Formula (I) compound to reach minimum inhibitory concentrations at the site of the metalloprotease to be inhibited, the personal attributes of the subject (such as weight), compliance with the treatment regimen, and the presence and severity of any side effects of the treatment.

Typically, for a human adult (weighing approximately 70 kilograms), from about 5 mg to about 3000 mg, more preferably from about 5 mg to about 1000 mg, more preferably from about 10 mg to about 100 mg, of Formula (I) compound are administered per day for systemic administration. It is understood that these dosage ranges are by way of example only, and that daily administration can be adjusted depending on the factors listed above.

A preferred method of administration for treatment of rheumatoid arthritis is oral or parenterally via intra-articular injection. As is known and practiced in the art, all formulations for parenteral administration must be sterile. For mammals, especially humans, (assuming an approximate body weight of 70 kilograms) individual doses of from about 10 mg to about 1000 mg are preferred.

A preferred method of systemic administration is oral. Individual doses of from about 10 mg to about 1000 mg, preferably from about 10 mg to about 300 mg are preferred.

Topical administration can be used to deliver the Formula (I) compound systemically, or to treat a subject locally. The amounts of Formula (I) compound to be topically administered depends upon such factors as skin sensitivity, type and location of the tissue to be treated, the composition and carrier (if any) to be administered, the particular Formula (I) compound to be administered, as well as the particular disorder to be treated and the extent to which systemic (as distinguished from local) effects are desired.

The inhibitors of the invention can be targeted to specific locations where the metalloprotease is accumulated by using targeting ligands. For example, to focus the inhibitors to metalloprotease contained in a tumor, the inhibitor is conjugated to an antibody or fragment thereof which is immunoreactive with a tumor marker as is generally understood in the preparation of immunotoxins in general. The targeting ligand can also be a ligand suitable for a receptor which is present on the tumor. Any targeting ligand which specifically reacts with a marker for the intended target tissue can be used. Methods for coupling the invention compound to the targeting ligand are well known and are similar to those described below for coupling to carrier. The conjugates are formulated and administered as described above.

For localized conditions, topical administration is preferred. For example, to treat ulcerated cornea, direct application to the affected eye may employ a formulation as eyedrops or aerosol. For corneal treatment, the compounds of the invention can also be formulated as gels, drops or ointments, or can be incorporated into collagen or a hydrophilic polymer shield. The materials can also be inserted as a contact lens or reservoir or as a subconjunctival formulation. For treatment of skin inflammation, the compound is applied locally and topically, in a gel, paste, salve or ointment. The mode of treatment thus reflects the nature of the condition and suitable formulations for any selected route are available in the art.

In all of the foregoing, of course, the compounds of the invention can be administered alone or as mixtures, and the compositions may further include additional drugs or excipients as appropriate for the indication.

Some of the compounds of the invention also inhibit bacterial metalloproteases although generally at a lower level than that exhibited with respect to mammalian metalloproteases. Some bacterial metalloproteases seem to be less dependent on the stereochemistry of the inhibitor, whereas substantial differences are found between diastereomers in their ability to inactivate the mammalian proteases. Thus, this pattern of activity can be used to distinguish between the mammalian and bacterial enzymes.

Preparation and Use of Antibodies

The invention compounds can also be utilized in immunization protocols to obtain antisera immunospecific for the invention compounds. As the invention compounds are relatively small, they are advantageously coupled to antigenically neutral carriers such as the conventionally used keyhole limpet hemocyanin (KLH) or serum albumin carriers. For those invention compounds having a carboxyl functionality, coupling to carrier can be done by methods generally known in the art. For example, the carboxyl residue can be reduced to an aldehyde and coupled to carrier through reaction with sidechain amino groups in protein-based carriers, optionally followed by reduction of imino linkage formed. The carboxyl residue can also be reacted with sidechain amino groups using condensing agents such as dicyclohexyl carbodiimide or other carbodiimide dehydrating agents.

Linker compounds can also be used to effect the coupling; both homobifunctional and heterobifunctional linkers are available from Pierce Chemical Company, Rockford, Ill. The resulting immunogenic complex can then be injected into suitable mammalian subjects such as mice, rabbits, and the like. Suitable protocols involve repeated injection of the immunogen in the presence of adjuvants according to a schedule which boosts production of antibodies in the serum. The titers of the immune serum can readily be measured using immunoassay procedures, now standard in the art, employing the invention compounds as antigens.

The antisera obtained can be used directly or monoclonal antibodies may be obtained by harvesting the peripheral blood lymphocytes or the spleen of the immunized animal and immortalizing the antibody-producing cells, followed by identifying the suitable antibody producers using standard immunoassay techniques.

The polyclonal or monoclonal preparations are then useful in monitoring therapy or prophylaxis regimens involving the compounds of the invention. Suitable samples such as those derived from blood, serum, urine, or saliva can be tested for the presence of the administered inhibitor at various times during the treatment protocol using standard immunoassay techniques which employ the antibody preparations of the invention.

The invention compounds can also be coupled to labels such as scintigraphic labels, e.g., technetium 99 or I-131, using standard coupling methods. The labeled compounds are administered to subjects to determine the locations of excess amounts of one or more metalloproteases in vivo. The ability of the inhibitors to selectively bind metalloprotease is thus taken advantage of to map the distribution of these enzymes in situ. The techniques can also be employed in histological procedures and the labeled invention compounds can be used in competitive immunoassays.

The following non-limiting examples illustrate the compounds, compositions, and uses of the present invention.

EXAMPLES

Compounds are analyzed using $^1$H and $^{13}$C NMR, Elemental analysis, mass spectra and/or IR spectra, as appropriate.

Typically inert solvents are used, preferably in dried form. For example, tetrahydrofuran (THF) is distilled from sodium and benzophenone, diisopropylamine is distilled from calcium hydride and all other solvents are purchased as the appropriate grade. Chromatography is performed on silica gel (70–230 mesh; Aldrich) or (230–400 mesh; Merck) as appropriate. Thin layer chromatography analysis (TLC) is performed on glass mounted silica gel plates (200–300 mesh; Baker) and visualized with UV or 5% phosphomolybdic acid in EtOH.

Example 1

Preparation of N-Hydroxy-2-[(4-methoxyphenylsulfonyl)amino]-3,3-dimethyl-3-methylthio-propanamide

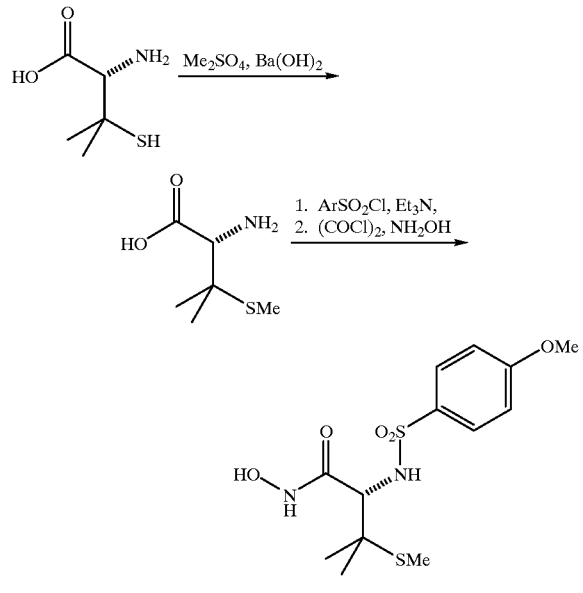

S-methyl-D-penicillamine

A suspension of D-Penicillamine (10.0 g, 67.01 mmol) in 0.4N solution of barium hydroxide octahydrate (330 mL, 67.01 mmol) is chilled on an ice water bath. Dimethyl sulfate (6.6 mL, 70.36 mmol, 1.05 equiv) is added dropwise over a period of 30 minutes. The suspension stirred for 18 hours at room temperature. A solution of 1 N sulfuric acid is added to the solution (pH~2) to precipitate out the barium sulfate. The supernatent is decanted and the precipitate is washed several times with water. The pH of the supernatent is adjusted to 6 with concentrated ammonium hydroxide and the water is evaporated off to give a pure white solid (10.9 g, 100% yield).

2-[(4-Methoxyphenylsulfonyl)amino]-3,3-dimethyl-3-methylthio-propionic acid

The penicillamine adduct (10.9 g, 67.01 mmol) is dissolved in dioxane (100 mL) and water (100 mL) and the resulting mixture is then stirred at room temperature. Triethylamine (50 mL, 670 mmol) is added to the reaction mixture followed by 4-methoxyphenylsulfonyl chloride (16.62 g, 80.41 mmol). The resulting homogeneous solution is stirred at room temperature for 18 hours and then acidified to pH~2 with 1N HCl. The solution is poured into water and extracted with methylene chloride. The organic extracts are dried (MgSO$_4$) and concentrated to an oil under reduced pressure . Purification is performed on a silica gel column eluting with 15% methanol and 85% chloroform giving a solid (73%).

N-Hydroxy-2-[(4-methoxyphenylsulfonyl)amino]-3,3-dimethyl-3-methylthio-propanamide The carboxylic acid (7.9 g, 23.7 mmol) in dichloromethane (100 mL) is stirred at room temperature and then oxalyl chloride (6.17 g, 48.6 mmol, 2.05 equiv) and DMF (1.73 g, 23.7 mmol) are added. The resulting solution is stirred at room temperature for 15 minutes. In a separate flask, hydroxylamine hydrochloride (6.5 g, 94.8 mmol, 4 equiv) in THF (35 mL) and water (10 mL) is stirred at 0° C. Triethylamine (14.3 g, 142.2 mmol, 6 equiv) is added and the resulting solution is stirred at 0° C. for 10 minutes. The acid chloride solution is added to the hydroxylamine solution at 0° C. and the resulting mixture is allowed to stir overnight at room temperature. The reaction mixture is acidified with 1 N HCl and then extracted with dichloromethane. The organic extracts are dried (Na$_2$SO$_4$) and concentrated to a solid under reduced pressure. The solid is recrystallized from chloroform to provide a white powder (65%). MS (ESI): 349 (M+H$^+$).

Example 2

The following compounds are prepared similarly to Example 1:

N-Hydroxy-2-[(4-bromophenylsulfonyl)amino]-3,3-dimethyl-3-methylthio-propanamide MS (ESI): 397, 399 (M+H$^+$).

N-Hydroxy-2-[(4-butoxyphenylsulfonyl)amino]-3,3-dimethyl-3-methylthio-propanamide MS (ESI): 391 (M+H$^+$).

Example 3

Preparation of N-Hydroxy-S,S-dioxo-2-[(4-methoxyphenylsulfonyl)amino]-3,3-dimethyl-3-methylthio-propanamide

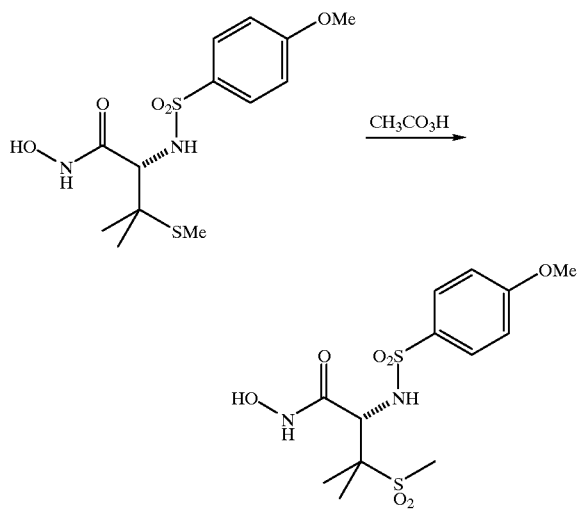

N-Hydroxy-S,S-dioxo-2-[(4-methoxyphenylsulfonyl)amino]-3,3-dimethyl-3-methylthio-propanamide The hydroxamic acid sulfide (4.0 g, 11.5 mmol) is dissolved in chloroform (50 mL). The suspension is cooled to 0° C. and then peracetic acid (32% Aldrich solution) (7.24 mL, 34.4 mmol, 3.0 equiv) is added. The solution becomes clear upon the addition of peracetic acid. The reaction mixture is then warmed to room temperature and the solution becomes a suspension again (cloudy). After several hours the reaction is checked by HPLC to monitor completion. Upon completion, the peracetic acid is removed by evaporation at reduced pressure and the resulting solid is purified by recrystallization with chloroform. MS (ESI): 381 (M+H$^+$).

Example 4

Preparation of N-Hydroxy-2-[(4-methoxybenzenesulfonyl)amino]-3,3-dimethyl-3-(p-methoxybenzenethio)-propanamide

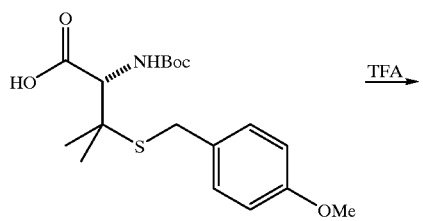

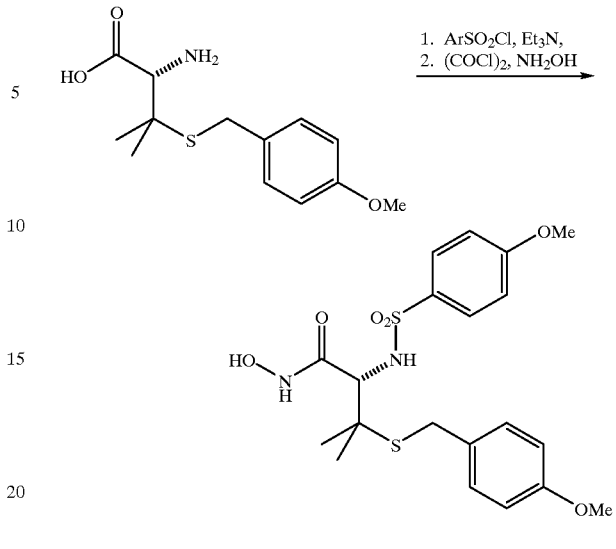

S-(4-methoxybenzyl)-D-penicillamine

The N-t-butoxycarbonyl-S-(4-methoxybenzyl)-D-penicillamine (5.0 g, 13.5 mmol) is dissolved in 40 mL of methylene chloride and cooled to 0° C. in an ice bath. Trifluoroacetic acid (18.5 g, 162 mmol) is added next, and the resulting mixture is stirred at 0° C. for 1 hour. The reaction mixture is warmed to room temperature and stirred until the starting material disappeared by TLC and mass spec (3 h.). The trifluoroacetic acid and methylene chloride are evaporated under reduced pressure to give the desired product.

N-[(4-methoxyphenyl)sulfonyl]-S-(4-methoxybenzyl)-D-penicillamine

The penicillamine adduct (3.65 g, 13.5 mmol) is then dissolved in dioxane (50 mL) and water (50 mL) and stirred at room temperature. Triethylamine (9.42 mL, 67.7 mmol) is added to the reaction mixture followed by 4-methoxyphenylsulfonyl chloride (3.37 g, 16.32 mmol). The resulting homogeneous solution is stirred at room temperature for 18 hours and then acidified to pH~2 with 1N HCl. The solution is poured into water and extracted with methylene chloride. The organic extracts are dried (MgSO$_4$) and concentrated to an oil under reduced pressure Purification is performed on a silica gel column eluting with 15% methanol and 85% chloroform giving a solid (73%).

N-Hydroxy-2-[(4-methoxybenzenesulfonyl)amino]-3,3-dimethyl-3-(p-methoxybenzenethio)-propanamide The carboxylic acid (2.5 g, 5.6 mmol) in dichloromethane (30 mL) is stirred at room temperature and then oxalyl chloride (1.0 mL, 11.48 mmol, 2.05 equiv) and DMF (0.4 mL, 5.6 mmol) are added. The resulting solution is stirred at room temperature for 15 minutes. In a separate flask, hydroxylamine hydrochloride (1.55 g, 22.4 mmol, 4 equiv) in THF (15 mL) and water (5 mL) is stirred at 0° C. Triethylamine (3.39 g, 33.6 mmol, 6 equiv) is added and the resulting solution is stirred at 0° C. for 10 minutes. The acid chloride solution is next added to the hydroxylamine solution at 0° C. and the resulting mixture is allowed to stir overnight (although usually done in 1–2 hours) at room temperature. The reaction mixture is next acidified with 1 N HCl and then extracted with dichloromethane. The organic extracts are dried (Na$_2$SO$_4$) and concentrated to a solid under reduced pressure. The solid is purified on reverse phase HPLC. MS (ESI): 455 (M+H$^+$).

Example 5

Preparation of N-hydroxy-a-[(4-methoxyphenyl) sulfonylamino]-tetrahydro-4-methylthio-cyclohexane-4-acetamide

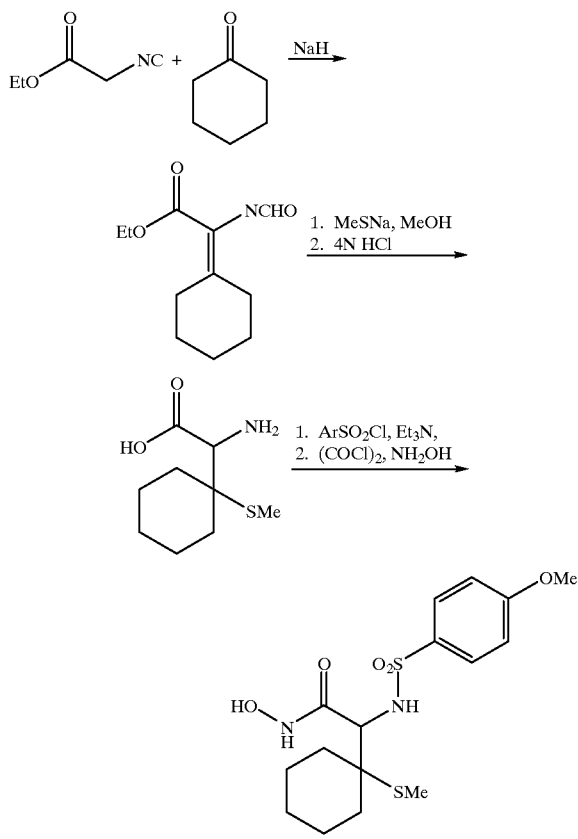

Ethyl N-formyl-a-cyclohexylideneglycinate

A suspension of sodium hydide (4.07 g, 60%, 101 mmol) in THF (100) is cooled to 0° C. Two addition funnels are charged with ethyl isocyanoacetate (10.0 g, 88.4 mmol) in THF (10 mL) and cyclohexanone (9.67 g, 88.4 mmol) in THF (10 mL). The solutions are added dropwise to the reaction mixture over a 30 minute period. The resulting mixture is then allowed to warm to room temperature and stirred overnight. The reaction mixture is quenched by the addition of saturated ammonium chloride solution. The layers are separated, and the aqueous layer is washed with ethyl acetate (3×100 mL). The combined organic extracts are washed with brine (200 mL), dried (MgSO$_4$) and then concentrated to an oil under reduced pressure. Ethyl acetate (40 mL) followed by hexane is added to the mixture until the mixture became turbid. The resulting solution is cooled to 0° C. and the desired product crystallized out of solution.

Ethyl N-formyl-a-amino-1-methylthio-cyclohexaneacetate

The cyclohexylidene (1 g, 4.74 mmol) in methanol (25 mL) is stirred at room temperature and then sodium thiomethoxide (0.66 g, 9.5 mmol, 2 equiv) is added. The resulting mixture is stirred at room temperature overnight. The reaction is quenched by the addition of saturated sodium bicarbonate solution. The resulting mixture is extracted with methylene chloride (3×100 mL). The organic extracts are dried (MgSO$_4$) and then concentrated to an oil under reduced pressure. The product is purified by chromatography on silica gel (7/3 EtOAC/hexane as eluent) to obtain the desired product as a clear colorless oil.

α-Amino-1-methylthio-cyclohexaneacetic acid

The formate ester (0.6 g, 2.44 mmol) is stirred in 4 N HCl (50 mL) and heated to reflux overnight. The reaction mixture is then cooled to room temperature and then the solvent is removed under reduced pressure to leave the desired product as a white solid.

α-[(4-Methoxyphenyl)sulfonylamino]-tetrahydro-1-methylthio-cyclohexaneacetic acid The amino acid (0.59 g, 2.44 mmol) in dioxane (20 mL) and water (20 mL) is stirred at room temperature and then triethylamine followed by 4-methoxyphenylsulfonyl chloride (0.53 g, 2.56 mmol, 1.05 equiv) is added. The resulting mixture is stirred at room temperature overnight. The reaction mixture is acidified with 1N HCl and then extracted with methylene chloride. The organic extracts are dried (MgSO$_4$) and then concentrated to an oil under reduced pressure. The oil is purified by chromatography on silica gel using 1/1 hexane/EtOAc as the eluent. The product is obtained as a colorless oil.

N-hydroxy-a-[(4-methoxyphenyl)sulfonylamino]-tetrahydro-4-methylthio-cyclohexane-4-acetamide The carboxylic acid (0.47 g, 1.26 mmol) in dichloromethane (10 mL) is stirred at room temperature and then oxalyl chloride (0.33 g, 2.58 mmol, 2.05 equiv) and DMF (92 mg, 1.26 mmol) are added. The resulting solution is stirred at room temperature for 15 minutes. In a separate flask, hydroxylamine hydrochloride (0.35 g, 5.04 mmol, 4 equiv) in THF (15 mL) and water (5 mL) is stirred at 0° C. Triethylamine (0.76 g, 7.56 mmol, 6 equiv) is added and the resulting solution is stirred at 0° C. for 10 minutes. The acid chloride solution is next added to the hydroxylamine solution at 0° C. and the resulting mixture is allowed to stir overnight at room temperature. The reaction mixture is next acidified with 1 N HCl and then extracted with dichloromethane. The organic extracts are dried (Na$_2$SO$_4$) and concentrated to a solid under reduced pressure. The product is recrystallized from chloroform. MS (ESI): 389 (M+H$^+$).

Example 6

The following compounds are prepared similarly to Example 5:

N-hydroxy-α-[(4-methoxyphenyl)sulfonylamino]-tetrahydro-4-methylthio-2H-pyran-4-acetamide MS (ESI): 391 (M+H$^+$).
N-hydroxy-α-[(4-methoxyphenyl)sulfonylamino]-tetrahydro-4-methylthio-2H-thiopyran-4-acetamide MS (ESI): 407 (M+H$^+$).
N-hydroxy-α-[(4-methoxyphenyl)sulfonylamino]-tetrahydro-4-methylthio-1-methyl-piperidine-4-acetamide MS (ESI): 404 (M+H$^+$).
N-hydroxy-α-[(4-bromophenyl)sulfonylamino]-tetrahydro-4-methylthio-cyclohexane-4-acetamide MS (ESI): 437, 439 (M+H$^+$).

N-hydroxy-α-[(4-butoxyphenyl)sulfonylamino]-tetrahydro-4-methylthio-cyclohexane-4-acetamide MS (ESI): 431 (M+H+).

Example 7

Preparation of N-Hydroxy-S,S-dioxo-α-[(4-methoxyphenyl)sulfonylamino]-tetrahydro-4-methylthio-cyclohexane-4-acetamide

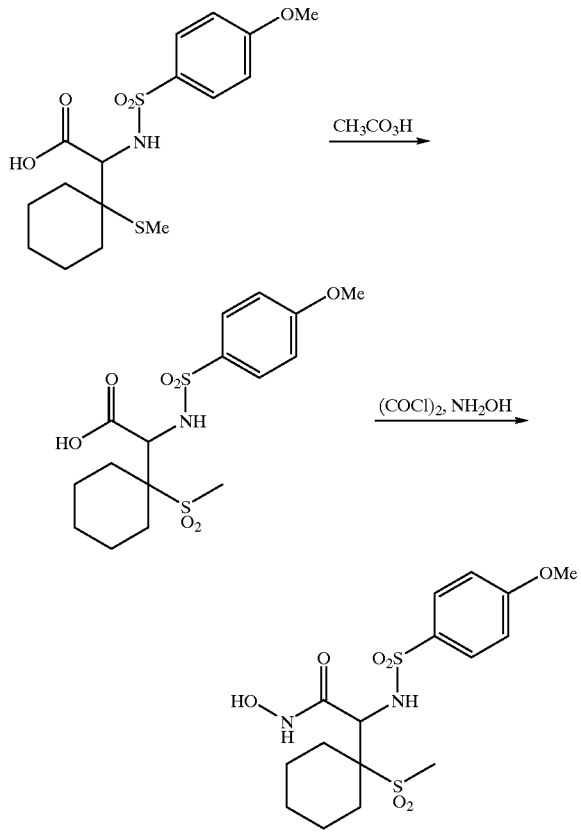

S,S-Dioxo-α-[(4-methoxyphenyl)sulfonylamino]-tetrahydro-4-methylthio-cyclohexaneacetic acid The hydroxamic acid sulfide (0.5 g, 1.34 mmol) is dissolved in chloroform (50 mL). The suspension is cooled to 0° C. and then peracetic acid (32% Aldrich solution) (1.3 mL, 5.04 mmol, 4.0 equiv) is added. The solution becomes clear upon the addition of peracetic acid. The reaction mixture is then warmed to room temperature and the solution becomes a suspension again (cloudy). After several hours the reaction is checked by HPLC to monitor completion. Upon completion, the peracetic acid is removed by evaporation at reduced pressure to leave the desired product as a white solid.

N-Hydroxy-S,S-dioxo-α-[(4-methoxyphenyl)sulfonylamino]-tetrahydro-4-methylthio-cyclohexane-4-acetamide The carboxylic acid (0.5 g, 1.24 mmol) in dichloromethane (10 mL) is stirred at room temperature and then oxalyl chloride (0.32 g, 2.53 mmol, 2.05 equiv) and DMF (90 mg, 1.24 mmol) are added. The resulting solution is stirred at room temperature for 15 minutes. In a separate flask, hydroxylamine hydrochloride (0.35 g, 4.96 mmol, 4 equiv) in THF (15 mL) and water (5 mL) is stirred at 0° C. Triethylamine (0.75 g, 7.44 mmol, 6 equiv) is added and the resulting solution is stirred at 0° C. for 10 minutes. The acid chloride solution is next added to the hydroxylamine solution at 0° C. and the resulting mixture is allowed to stir overnight at room temperature. The reaction mixture is next acidified with 1 N HCl and then extracted with dichloromethane. The organic extracts are dried ($Na_2SO_4$) and concentrated to a solid under reduced pressure. The product is recrystallized from chloroform. MS (ESI): 421 (M+H+).

Example 8

The following compounds are prepared similarly to Example 7:

N-hydroxy-S,S-dioxo-α-[(4-methoxyphenyl)sulfonylamino]-tetrahydro-4-methylthio-2H-pyran-4-acetamide MS (ESI): 423 (M+H+).
N-hydroxy-S,S,S,S-tetraoxo-α-[(4-methoxyphenyl)sulfonylamino]-tetrahydro-4-methylthio-2H-thiopyran-4-acetamide MS (ESI): 455 (M+H+).
N-hydroxy-S,S-dioxo-α-[(4-methoxyphenyl)sulfonylamino]-tetrahydro-4-methylthio-1-methyl-piperidine-4-acetamide MS (ESI): 436 (M+H+).
N-hydroxy-S,S-dioxo-α-[(4-bromophenyl)sulfonylamino]-tetrahydro-4-methylthio-cyclohexane-4-acetamide MS (ESI): 469, 471 (M+H+).
N-hydroxy-S,S-dioxo-α-[(4-butoxyphenyl)sulfonylamino]-tetrahydro-4-methylthio-cyclohexane-4-acetamide MS (ESI): 463 (M+H+).

Example 9

Preparation of N-hydroxy 2R-[(4-methoxyphenyl)sulphonylamino]succinamic acid propyl ester

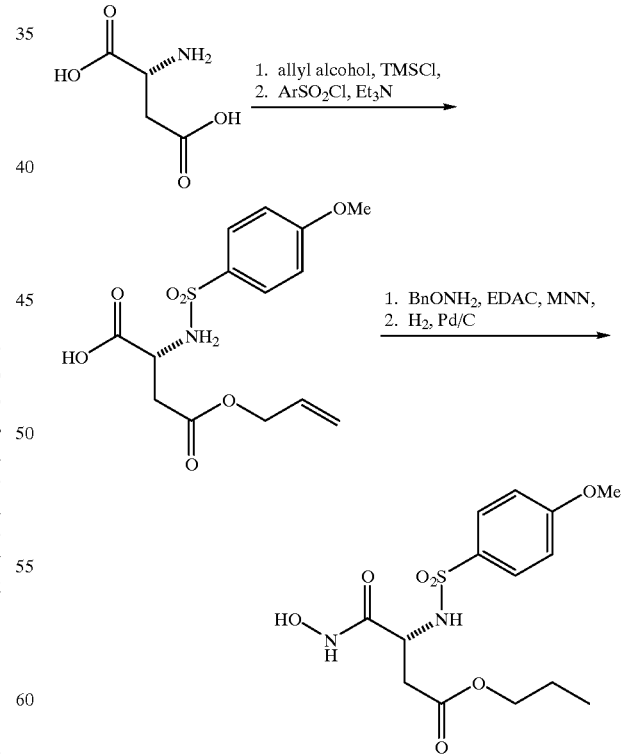

D-Aspartic acid γ-allyl ester hydrochloride

D-Aspartic acid (4 g) is suspended in allyl alcohol (100 mL) and trimethylsilyl chloride (9.5 mL) is added dropwise and the reaction mixture is stirred at room temperature for 20 hours. Ether (600 mL) is added and the white precipitate is collected by filtration, eashed with ether and dried to give D-aspartic acid γ-allyl ester hydrochloride.

N-[(4-Methoxyphenyl)sulphonyl-D-aspartic acid γ-allyl ester

D-Aspartic acid γ-allyl ester hydrochloride (1.6 g) is dissolved in dioxane-water (1:1 v/v, 40 mL) and the solution is cooled to 0° C. Triethylamine (2.8 mL) is added followed by p-methoxysulfonyl chloride (1.65 g) and the reaction mixture is stirred at 0° C. for 15 minutes then at room temperature for 4 hours. The reaction mixture is concentrated and the residue is partitioned between 1N hydrochloric acid and ethyl acetate. The aqueous phase is washed with ehtyl acetate. The combined organic phases are washed with aqueous sodium bicarbonate, with brine, dried ($Na_2SO_4$) and concentrated under reduced pressure to give N-[(4-methoxyphenyl)sulphonyl-D-aspartic acid γ-allyl ester as a white solid.

N-Benzyloxy 2R-[(4-methoxyphenyl) sulphonylamino]succinamic acid allyl ester N-[(4-Methoxyphenyl)sulphonyl-D-aspartic acid γ-allyl ester (3.43 g) is dissolved in N,N-dimethylformamide (20 mL) and the solution is cooled to 0° C. 1-Hydroxybenzotriazole (4.6 g), N-methylmorpholine (3.3 mL) and 1-ethyl-3-(3-dimethylaminopropyl)carbodiimide (2.3 g) are sequentially added followed, after 20 minutes, with O-benzylhydroxylamine hydrochloride (1.6 g). The reaxtion mixture is stirred at room temperature for 20 hours and water is slowly added. The precipitate is collected and washed with water and dried under vacuo. The crude product is purified by crystalization from aqueous methanol to give N-benzyloxy 2R-[(4-methoxyphenyl)sulphonylamino] succinamic acid allyl ester as a white solid.

N-Hydroxy 2R-[(4-methoxyphenyl)sulphonylamino] succinamic acid propyl ester

N-Benzyloxy 2R-[(4-methoxyphenyl)sulphonylamino] succinamic acid allyl ester (150 mg) is dissolved in methanol (10 mL) and palladium on carbon catalyst (20 mg) is added. The reaction mixture is stirred under atmospheric pressure of hydrogen for 1.5 hours. The catalyst is removed by filtration through celite, the solvents are removed under reduced pressure and the crude product is purified by crystallization from ethyl acetate to give N-hydroxy 2R-[(4-methoxyphenyl)sulphonylamino]succinamic acid propyl ester as a white solid. MS (ESI): 361 (M+H$^+$), 378 (M+NH$_4^+$).

Example 10

Preparation of 2-[(4-methoxyphenyl) sulfonylamino]-isobutyric hydroxamic acid

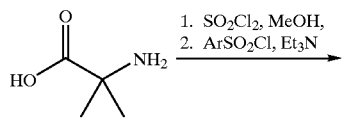

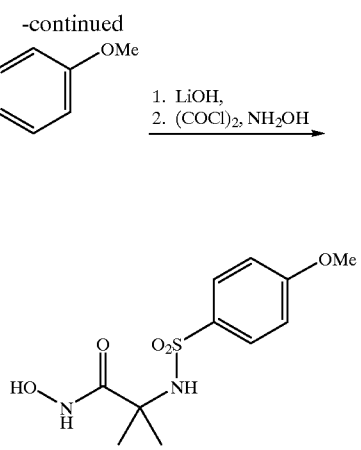

2-[(4-methoxyphenyl)sulfonylamino]-isobutyric acid methyl ester

2-Amino-isobutyric acid (15 g, 0.15 mole) was taken in 500 mL and treated with $SOCl_2$ (37 mL, 50 mmol), and stirred for 18 hrs. The mixture was then evaporated to dryness to give 74 g (81%) of white solid.

The above solid (5.0 g, 43 mmol) was dissolved in water : dioxane (1:1, 40 mL) with triethylamine (15 mL, 107 mole). 4-Methoxyphenylsulfonyl chloride (9.7 g, 0.47 mole) was added and the mixture was stirred 14 hr. at room temperature. The mixture was then partitioned between EtOAc and 1N HCl. Layers were separated and the organic layer was washed 1× with 1N HCl, 1× with brine, dried over MgSO$_4$, filtered and evaparated to give 8 g of yellow oil. The mixture was then chromatographed over flash silica with hexane:EtOAc (8:2) to give 2.8 g (23%) of white powder. MS(CI) 288 (M$^+$+H, 100%), 305 (62), 228 (71), 171 (26), 118 (15).

2-[(4-methoxyphenyl)sulfonylamino]-isobutyric hydroxamic acid

The starting ester (500 mg, 1.74 mmol) was taken in dioxane:water (1:1, 5 mL) and treated with LiOH (146 mg, 3.5 mmol) and stirred 18 hrs at room temrerature. The mixture was then partitioned between 1N HCl and EtOAc. The organic layer was then washed with brine, dried over MgSO$_4$, filtered and concentrated to give a white solid.

The above acid was dissolved in 18 mL of $CH_2Cl_2$ at room temperature and treated with (COCl)$_2$ and catalytic DMF and stirred for 1 hr. In a separate flask, hydroxyl amine HCl (512 mg, 7.32 mmole) was stirred in water:THF (3:8, 11 mL), cooled to 0° C., and treated with triethyl amine. The acid chloride solution was added to the hydroxyl amine solution at 0° C., allowed to come to room temperature and stirred for 18 hrs. The mixture was partitioned between 1N HCl and $CH_2Cl_2$. The organic layer was then dried over MgSO$_4$, filtered and evaparated to give crude material which was chromatographed over flash silica with EtOAc to give 154 mg of desired hydroxamic acid. MS (ESI) 274 (M$^+$+H, 58), 291 (100).

Example 11

Preparation of 2-[(N)-(4-methoxyphenyl)sulfonyl-(N)-allylamino]-isobutyric hydroxamic acid

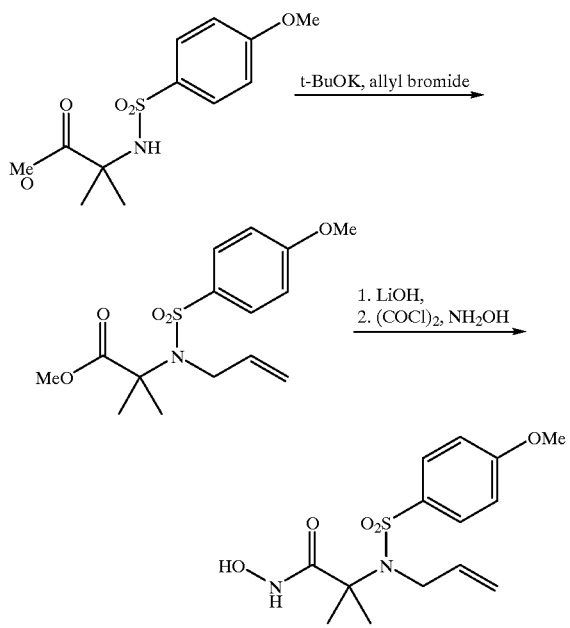

2-[(N)-(4-methoxyphenyl)sulfonyl-(N)-allylamino]-isobutyric acid methyl ester

The starting sulfonamide (600 mg, 2.09 mmole), was taken in 10 mL of dry THF at room temperature and treated with tert-butoxide (2.3 mL, 1 M in THF, 2.3 mmole) and stirred for 1 hr which resulted in the formation of a thick precipitate. Allyl bromide (271 mL, 3.2 mmole) was added and the mixture heated to 50° C. for 3 hr which resulted in the formation of a major and a minor product. The mixture was partitioned between 1N HCl and ether. The organic layer was dried over $MgSO_4$, filtered and evaparated. The residue was chromatographed over flash silica with hexane:EtOAc (3:1 to 1:1) to give 413 mg of the desired alkylated sulfonamide as well as 91 mg of the same product which had undergone trans esterification to an allyl ester. MS (CI) 288 ($M^+$+H).

2-[(N)-(4-methoxyphenyl)sulfonyl-(N)-allylamino]-isobutyric hydroxamic acid

The starting ester (257 mg, 0.782 mmol) was taken in dioxane:water (1:1, 3 mL) and treated with LiOH (73 mg, 1.7 mmol) and stirred 18 hrs at room temrerature. The mixture was then partitioned between 1N HCl and EtOAc. The organic layer was then washed with brine, dried over $MgSO_4$, filtered and concentrated to give a white solid.

The above acid was dissolved in 3 mL of $CH_2Cl_2$ at room temperature and treated with $(COCl)_2$ (140 mL, 1.6 mmole) and catalytic DMF and stirred for 1 hr. In a separate flask, hydroxyl amine HCl (512 mg, 7.32 mmole) was stirred in water:THF (1:3, 4 mL), cooled to 0° C., and treated with 653 mL of triethyl amine. The acid chloride solution was added to the hydroxyl amine solution at 0° C., allowed to come to room temperature and stirred for 18 hrs. The mixture was partitioned between 1N HCl and $CH_2Cl_2$. The organic layer was then dried over $MgSO_4$, filtered and evaparated to give crude material which was chromatographed over flash silica with EtOAc to give 26 mg of desired hydroxamic acid. MS (ESI) 289 (M++H, 44), 306 (100).

Example 12

Preparation of N-Hydroxy-2-[(4-methoxyphenyl)sulfonylamino]-4-phthalimido-butanamide

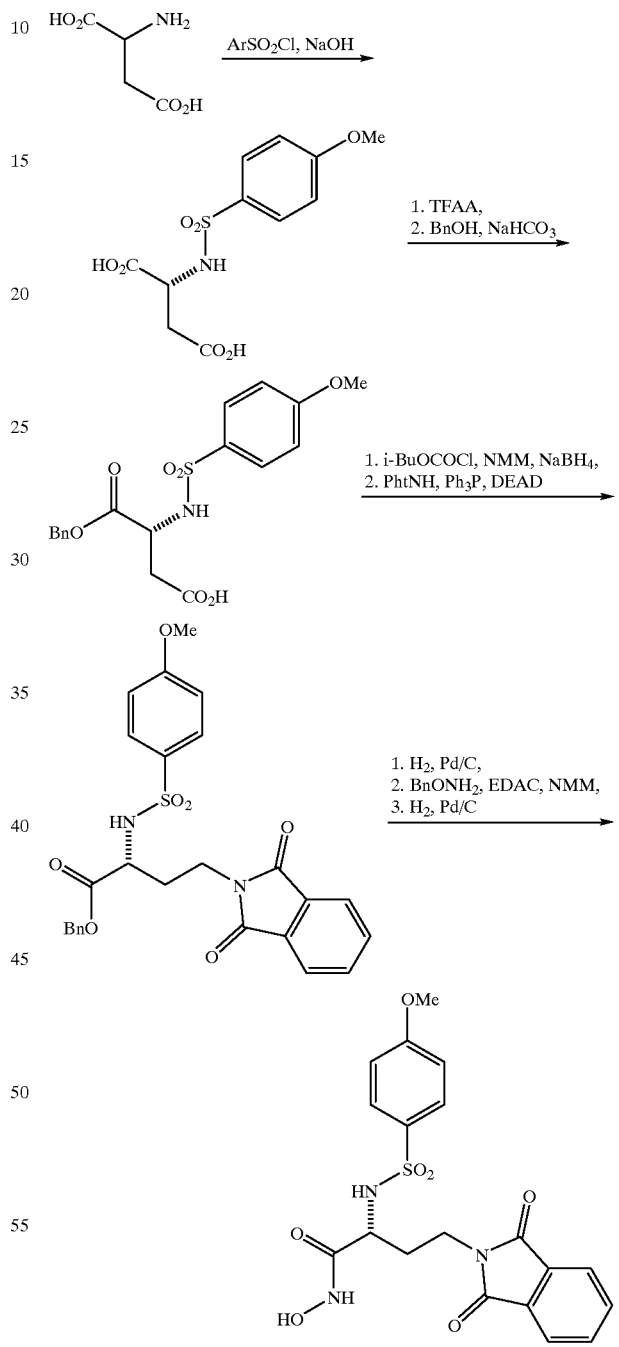

N-[4-Methoxyphenyl)sulfonyl]-D-aspartic acid

D-Aspartic acid (2.66 g) is suspended in 2N NaOH (30 mL) and 4-methoxyphenylsulfonyl chloride (4.12 g) is added. The mixture is stirred at 70° C. for 5 hours (clear solution), cooled down to room temperature and extracted with methylene chloride. The aqueous phase, after acidifying with 12N HCl, is extracted with ethyl acetate. The combined organic phases are with brine, dried (Na$_2$SO$_4$) and concentrated under reduced pressure to give N-[4-methoxyphenyl)sulfonyl]-D-aspartic acid as a white solid.

N-[(4-Methoxyphenyl)sulphonyl-D-aspartic acid α-benzyl ester

N-[4-Methoxyphenyl)sulfonyl]-D-aspartic acid (4.55 g) is dissolved in dry tetrahydrofurane (40 mL) and trifluoroacetic anhydride (20 mL) is added. The reaction mixture is stirred for 20 hours and the volatiles are removed under reduced pressure. The crude anhydride is dissolved in benzyl alcohol (32 mL) and the mixture is stirred for 20 hours at room temperature. Saturated sodium bicarbonate is added and the mixture is vigorously stirred and then extracted with ethyl ether. The aqueous phase is acidified with 6N hydrochloric acid and exteracted with ethyl acetate. The combined organic phases are washed with aqueous sodium bicarbonate, with brine, dried (Na$_2$SO$_4$) and concentrated under reduced pressure to give N-[(4-methoxyphenyl) sulphonyl-D-aspartic acid α-benzyl ester as a white solid.

Benzyl 2-[(4-methoxyphenyl)sulfonylamino]-4-phthalimido-butanoate

N-[(4-Methoxyphenyl)sulphonyl-D-aspartic acid α-benzyl ester (400 mg) is dissolved in dimethoxyethane (2 mL) and cooled to 0° C. N-methyl morpholine (112 μL) and isobutyl chloroformate (132 μL) are sequentially added followed by sodium borohydride (115 mg) and water (25 mL). The product is extracted with ethyl acetate and the combined organic phases are washed with aqueous sodium bicarbonate, with brine, dried (Na$_2$SO$_4$) and concentrated under reduced pressure. The crude alcohol, phthalimide (197 mg) and triphenylphosphine (352.5 mg) are dissolved in dry tetrahydrofuran (11 mL). The solution is cooled to 0° C. and diethyl azadicarboxylate (212 μL) is added. The colling bath is removed and the solution is stirred for 18 hours. Ethyl acetate is added and the mixture is washed with brine, dried (Na$_2$SO$_4$) and concentrated under reduced pressure. The crude product is purified by crystallization to give benzyl 2-[(4-methoxyphenyl)sulfonylamino]-4-phthalimido-butanoate as colorless solid. MS (ESI) 509 (M+H)$^+$.

N-Hydroxy-2-[(4-methoxyphenyl)sulfonylamino]-4-phthalimido-butanamide

2-[(4-methoxyphenyl)sulfonylamino]-4-phthalimido-butanoate (199 mg) is dissolved in ethyl acetate-methanol mixture (6 mL, 2:1 v/v) and palladium catalyst (10% Pd/C) is added. The mixture is stirred under the atmosphere of hydrogen for 3 hours, filtered through a plug of Celite and the volatiles are removed under reduced pressure to give the crude carboxylic acid. Following the procedure described in Example 9, it is converted to the corresponding hydroxamic acid to give N-hydroxy-2-[(4-methoxyphenyl) sulfonylamino]-4-phthalimido-butanamide as a colorless solid. MS (ESI) 434 (M+H)$^+$.

Example 13

Preparation of aminoacid-based hydroxamic acid

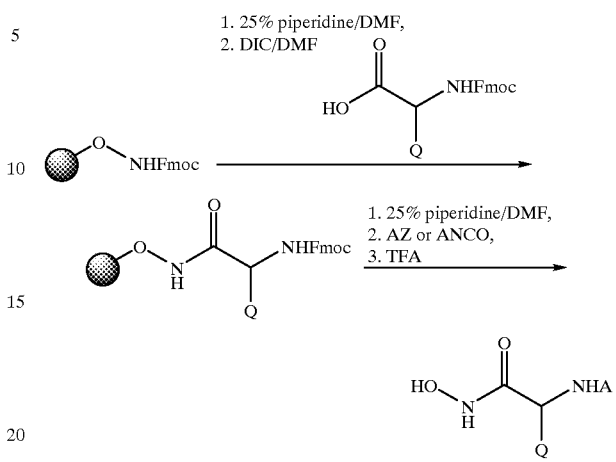

Fmoc Deprotection of Resin Bound N-(Fmoc) hydroxylamine (1)

2-Chlorotrityl polystyrene resin functionalized with N-(Fmoc)hydroxylamine (1) (5.2 g, 4.0 mmol) was washed several times with dichloromethane (DCM). The resin was slurried in DCM (50 mL) and to this was added a solution of 25% piperdine in dimethylformamide (DMF) (15 mL). The resin slurry was agitated for 30 minutes then filtered. The resin was washed with DMF (4×75 mL). The resin was again treated with 25% piperdine in DMF in a manner similar to the previous. Following filtration, the resin was washed first with DMF (4×75 mL) then with DCM (2×75 mL) and methanol (MTH) (3×75 mL) in an alternating fashion. The resin was vacuum dried for 1 h.

The Fmoc deprotected resin was slurried in 1:1 DMF/DCM and delivered by volume to 96 wells of the ACT 496 MOS Robot. This gave approxamately 0.042 mmol of substrate per well. All subsequent procedures were preformed identically to each of the 96 wells unless otherwise noted.

Amino Acid Coupling to O-(Resin)hydroxylamine

O-(Resin)hydroxylamine (0.042 mmol) was treated with a solution of the appropriate (Table 1) N-(Fmoc) protected amino acid (6 eq.) in DMF (1.5 mL) containing 1,3-diisopropylcarbodiimide (6 eq.). The resulting slurry was agitated for 18 h. The resin was filtered and washed first with DMF (4×3 mL) then with DCM (2×3 mL) and methanol (MTH) (3×3 mL) in an alternating fashion.

α-N-Fmoc Deprotection of Resin Bound Amino Acid Hydroxamate (2)

O-(Resin)hydroxylamine-Amino Acid(α-N-Fmoc) (0.042 mmol) was slurried in a solution of 25% piperdine in DMF (1.5 mL). The resin slurry was agitated for 30 minutes then filtered. The resin was washed with DMF (4×3 mL). The resin was again treated with 25% piperdine in DMF in a manner similar to the previous. Following filtration, the resin was washed first with DMF (4×3 mL) then with DCM (2×3 mL) and MTH (3×3 mL) in an alternating fashion.

α-N-Functionalization (R) of Resin Bound Amino Acid Hydroxamate (3)

Formation of Sulfonamides

O-(Resin)hydroxylamine-Amino Acid (3) (0.042 mmol) was treated with the appropriate sulfonyl chloride (Table 1) (3 eq.) as a solution in 2:1 1,2-dichloroethane/diisopropylethylamine (1.5 mL) for 3 h.. The resin was filtered and washed first with DMF (4×3 mL) then with DCM (2×3 mL) and methanol (MTH) (3×3 mL) in an alternating fashion.

Formation of Caproic Acid Amides

O-(Resin)hydroxylamine-Amino Acid (3) (0.042 mmol) was treated with a solution of n-caproic acid (5 eq.), benzotriazole-1-yl-oxy-tris-pyrrolidino-phosphonium hexafluorophosphate (PyBOP) (5 eq.), and triethylamine (10.5 eq.) in DMF (1.5 mL). This slurry was allowed to agitate for 18 h. then filtered. Following filtration, the resin was washed first with DMF (4×3 mL) then with DCM (2×3 mL) and MTH (3×3 mL) in an alternating fashion.

Formation of Nicotinic and Benzoic Acid Amides

O-(Resin)hydroxylamine-Amino Acid (3) (0.042 mmol) was treated with a solution of the appropriate acid (5 eq.) and 1,3-diisopropylcarbodiimide (5 eq.) in DMF (1.5 mL). The resulting slurry was agitated for 18 h. and then filtered. Following filtration, the resin was washed first with DMF (4×3 mL) then with DCM (2×3 mL) and MTH (3×3 mL) in an alternating fashion.

Formation of Ureas

O-(Resin)hydroxylamine-Amino Acid (3) (0.042 mmol) was treated with a solution of p-tolylisocyanate (5 eq.) in 2:1 DMF/diisopropylethylamine. The resulting slurry was agitated for 18 h. and then filtered. Following filtration, the resin was washed first with DMF (4×3 mL) then with DCM (2×3 mL) and MTH (3×3 mL) in an alternating fashion.

Cleavage of the Hydroxamic Acid (4) from the Solid Support

The α-N-substituted resin bound Amino Acid hydroxamate (0.042 mmol) was treated with a solution of 25% trifluoroacetic acid in 1,2-dichloroethane (2 mL) for 20 min. after which time the resin was filtered and the filtrate was collected in pre-tared vials. The resin was washed with MTH (3 mL) and the washing was pooled with the original filtrate. The vials were evaporated to dryness then the contents of the vials were transferred to a deep well microtitre plate using dimethylsulfoxide (1 mL/well).

The following compounds are prepared using method described above:

N-Hydroxy-2-[(4-methoxyphenylsulfonyl)amino]-acetamide MS (ESI): 261(M+H$^+$).
N-Hydroxy-2-[(4-butoxyphenylsulfonyl)amino]-acetamide MS (ESI): 303 (M+H$^+$).
N-Hydroxy-2-[(4-bromophenylsulfonyl)amino]-acetamide MS (ESI): 309 (M+H$^+$).
N-Hydroxy-2-[octanoylamino]-acetamide MS (ESI): 217 (M+H$^+$).
N-Hydroxy-2-[nicotinoylamino]-acetamide MS (ESI): 196 (M+H$^+$).
N-Hydroxy-2-[benzoylamino]-acetamide MS (ESI): 195 (M+H$^+$).
N-Hydroxy-2-[[(4-methylphenylamino)carbonyl]amino]-acetamide MS (ESI): 224 (M+H$^+$).
(2R)-N-Hydroxy-[(4-methoxyphenylsulfonyl)amino]-propionamide MS (ESI): 275 (M+H$^+$).
(2R)-N-Hydroxy-[(4-butoxyphenylsulfonyl)amino]-propionamide MS (ESI): 317 (M+H$^+$).
(2R)-N-Hydroxy-[(4-bromophenylsulfonyl)amino]-propionamide MS (ESI): 323 (M+H$^+$).
(2R)-N-Hydroxy-[octanoylamino]-propionamide MS (ESI): 231 (M+H$^+$).
(2R)-N-Hydroxy-[nicotinoylamino]-propionamide MS (ESI): 210 (M+H$^+$).
(2R)-N-Hydroxy-[benzoylamino]-propionamide MS (ESI): 209 (M+H$^+$).
(2R)-N-Hydroxy-[[(4-methylphenylamino)carbonyl]amino]-propionamide MS (ESI): 238 (M+H$^+$).
(2R)-N-Hydroxy-[(4-methoxyphenylsulfonyl)amino]-3-methylbutanamide MS (ESI): 303 (M+H$^+$).
(2R)-N-Hydroxy-[(4-butoxyphenylsulfonyl)amino]-3-methylbutanamide MS (ESI): 345 (M+H$^+$).
(2R)-N-Hydroxy-[(4-bromophenylsulfonyl)amino]-3-methylbutanamide MS (ESI): 351 (M+H$^+$).
(2R)-N-Hydroxy-[octanoylamino]-3-methylbutanamide MS (ESI): 259 (M+H$^+$).
(2R)-N-Hydroxy-[nicotinoylamino]-3-methylbutanamide MS (ESI): 238 (M+H$^+$).
(2R)-N-Hydroxy-[benzoylamino]-3-methylbutanamide MS (ESI): 237 (M+H$^+$).
(2R)-N-Hydroxy-[[(4-methylphenylamino)carbonyl]amino]-3-methylbutanamide MS (ESI): 266 (M+H$^+$).
(2R)-N-Hydroxy-[(4-methoxyphenylsulfonyl)amino]-3-phenylpropionamide MS (ESI): 351 (M+H$^+$).
(2R)-N-Hydroxy-[(4-butoxyphenylsulfonyl)amino]-3-phenylpropionamide MS (ESI): 393 (M+H$^+$).
(2R)-N-Hydroxy-[(4-bromophenylsulfonyl)amino]-3-phenylpropionamide MS (ESI): 399 (M+H$^+$).
(2R)-N-Hydroxy-[octanoylamino]-3-phenylpropionamide MS (ESI): 307 (M+H$^+$).
(2R)-N-Hydroxy-[nicotinoylamino]-3-phenylpropionamide MS (ESI): 286 (M+H$^+$).
(2R)-N-Hydroxy-[benzoylamino]-3-phenylpropionamide MS (ESI): 285 (M+H$^+$).
(2R)-N-Hydroxy-[[(4-methylphenylamino)carbonyl]amino]-3-phenylpropionamide MS (ESI): 314 (M+H$^+$).
(2R)-N-Hydroxy-[(4-methoxyphenylsulfonyl)amino]-3-methylpropionamide MS (ESI): 289 (M+H$^+$).
(2R)-N-Hydroxy-[(4-butoxyphenylsulfonyl)amino]-3-methylpropionamide MS (ESI): 331 (M+H$^+$).
(2R)-N-Hydroxy-[(4-bromophenylsulfonyl)amino]-3-methylpropionamide MS (ESI): 337 (M+H$^+$).
(2R)-N-Hydroxy-[nicotinoylamino]-3-methylpropionamide MS (ESI): 224 (M+H$^+$).
(2R)-N-Hydroxy-[(4-methoxyphenylsulfonyl)amino]-4-methylthiobutanamide MS (ESI): 335 (M+H$^+$).
(2R)-N-Hydroxy-[(4-butoxyphenylsulfonyl)amino]-4-methylthiobutanamide MS (ESI): 377 (M+H$^+$)
(2R)-N-Hydroxy-[(4-bromophenylsulfonyl)amino]-4-methylthiobutanamide MS (ESI): 383 (M+H$^+$).
(2R)-N-Hydroxy-[octanoylamino]-4-methylthiobutanamide MS (ESI): 291 (M+H$^+$).
(2R)-N-Hydroxy-[nicotinoylamino]-4-methylthiobutanamide MS (ESI): 270 (M+H$^+$).
(2R)-N-Hydroxy-[benzoylamino]-4-methylthiobutanamide MS (ESI): 269 (M+H$^+$).
(2R)-N-Hydroxy-[[(4-methylphenylamino)carbonyl]amino]-4-methylthiobutanamide MS (ESI): 298 (M+H$^+$).
(2R)-N-Hydroxy-[(4-methoxyphenylsulfonyl)amino]-6-aminocapronamide MS (ESI): 332 (M+H$^+$).
(2R)-N-Hydroxy-[(4-butoxyphenylsulfonyl)amino]-6-aminocapronamide MS (ESI): 374 (M+H$^+$).
(2R)-N-Hydroxy-[(4-bromophenylsulfonyl)amino]-6-aminocapronamide MS (ESI): 380 (M+H$^+$).
(2R)-N-Hydroxy-[octanoylamino]-6-aminocapronamide MS (ESI): 288 (M+H$^+$).
(2R)-N-Hydroxy-[nicotinoylamino]-6-aminocapronamide MS (ESI): 267 (M+H$^+$).
(2R)-N-Hydroxy-[benzoylamino]-6-aminocapronamide MS (ESI): 266 (M+H$^+$).
(2R)-N-Hydroxy-[[(4-methylphenylamino)carbonyl]amino]-6-aminocapronamide MS (ESI): 295 (M+H$^+$).
N-Hydroxy-2-[nicotinoylamino]-cyclohexanecarbonamide MS (ESI): 264 (M+H$^+$).

N-Hydroxy-2-[(4-bromophenylsulfonyl)amino]-2,3-dihydro-1H-indene-2-carbonamide MS (ESI): 411 (M+H$^+$).

N-Hydroxy-2-[nicotinoylamino]-2,3-dihydro-1H-indene-2-carbonamide MS (ESI): 298 (M+H$^+$).

(2R)-N-Hydroxy-[(4-methoxyphenylsulfonyl)amino]-3-(3-pyridine)propionamide MS (ESI): 352 (M+H$^+$).

(2R)-N-Hydroxy-[(4-butoxyphenylsulfonyl)amino]-3-(3-pyridine)propionamide MS (ESI): 394 (M+H$^+$).

(2R)-N-Hydroxy-[(4-bromophenylsulfonyl)amino]-3-(3-pyridine)propionamide MS (ESI): 400 (M+H$^+$).

(2R)-N-Hydroxy-[octanoylamino]-3-(3-pyridine)propionamide MS (ESI): 308 (M+H$^+$).

(2R)-N-Hydroxy-[nicotinoylamino]-3-(3-pyridine)propionamide MS (ESI): 287 (M+H$^+$).

(2R)-N-Hydroxy-[benzoylamino]-3-(3-pyridine)propionamide MS (ESI): 286 (M+H$^+$).

(2R)-N-Hydroxy-[[(4-methylphenylamino)carbonyl]amino]-3-(3-pyridine)propionamide MS (ESI): 315 (M+H$^+$).

(2R)-N-Hydroxy-[(4-methoxyphenylsulfonyl)amino]-3-amidopropionamide MS (ESI): 318 (M+H$^+$).

(2R)-N-Hydroxy-[(4-butoxyphenylsulfonyl)amino]-3-amidopropionamide MS (ESI): 360 (M+H$^+$).

(2R)-N-Hydroxy-[(4-bromophenylsulfonyl)amino]-3-amidopropionamide MS (ESI): 366 (M+H$^+$).

(2R)-N-Hydroxy-[octanoylamino]-3-amidopropionamide MS (ESI): 274 (M+H$^+$).

(2R)-N-Hydroxy-[nicotinoylamino]-3-amidopropionamide MS (ESI): 253 (M+H$^+$).

(2R)-N-Hydroxy-[benzoylamino]-3-amidopropionamide MS (ESI): 252 (M+H$^+$).

(2R)-N-Hydroxy-[[(4-methylphenylamino)carbonyl]amino]-3-amidopropionamide MS (ESI): 281 (M+H$^+$).

(2R, 3S)-N-Hydroxy-[(4-methoxyphenylsulfonyl)amino]-3-hydroxybutanamide MS (ESI): 305 (M+H$^+$).

(2R, 3S)-N-Hydroxy-[(4-butoxyphenylsulfonyl)amino]-3-hydroxybutanamide MS (ESI): 347 (M+H$^+$).

(2R, 3S)-N-Hydroxy-[(4-bromophenylsulfonyl)amino]-3-hydroxybutanamide MS (ESI): 353 (M+H$^+$).

(2R, 3S)-N-Hydroxy-[octanoylamino]-3-hydroxybutanamide MS (ESI): 261 (M+H$^+$).

(2R, 3S)-N-Hydroxy-[nicotinoylamino]-3-hydroxybutanamide MS (ESI): 240 (M+H$^+$).

(2R, 3S)-N-Hydroxy-([benzoylamino]-3-hydroxybutanamide MS (ESI): 239 (M+H$^+$).

(2R, 3S)-N-Hydroxy-[[(4-methylphenylamino)carbonyl]amino]-3-hydroxybutanamide MS (ESI): 268 (M

Example 14

Preparation of substituted 2,3-diaminopropionic hydroxamic acid

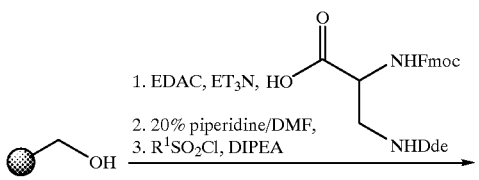

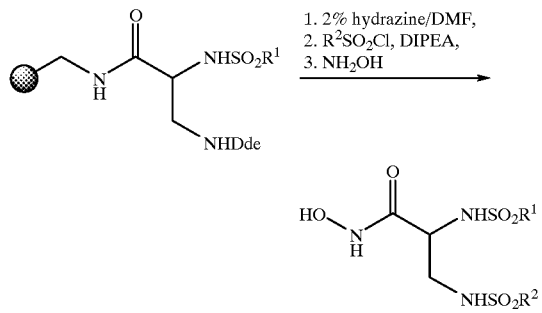

Loading of Wang Resin with Nα-(Fmoc))-Nβ-(Dde)-diaminopropionic acid

Wang resin (Advanced Chemtech, 0.84 mmol/g, 5.0 g, 4.2 mmol) was slurried in dry dichloromethane (75 mL). To this was added Nα-(Fmoc))-Nβ-(Dde)-diaminopropionic acid (3.1 g, 6.3 mmol) followed by triethylamine (0.9 mL, 6.3 mmol) and 1-(3-dimethylaminopropyl)-3-ethylcarbodiimide hydrochloride (1.2 g, 6.3 mmol). The mixture was agitated until all of the components were dissolved at which point hydroxybenzotriazole (0.1 g, 0.63 mmol) was added and the slurry was shaken for 23 h. The resin was filtered and washed with several portions of dichloromethane and methanol. The resin was vacuum dried for 16 h. Yield and new loading values were determined by cleavage of a small amount of the derivitized resin (0.036 g) with 95% TFA/H$_2$O. Yield 10 mg (95%), MS m/z 491 [M+H]$^+$. The new loading value was determined to be 0.601 mmol/g. The previously loaded resin was transfered to the 96 well reaction block of the Advanced Chemtech 496 MOS Robot. To each of 80 wells was added functionalized resin (0.050 g, 0.03 mmol). All of the subsequent procedures were preformed on each of the 80 wells.

Fmoc deprotection: The resin was slurried in N,N-dimethylformamide (0.5 mL) and to this was added a 20% solution of piperdine in DMF (1.5 mL). The reaction was agitated for 20 minutes and then the resin was filtered. This protocol was repeated one additional time. Following the final filtration, the resin was washed with DMF (2×2 mL). The resin was then washed twice each with DCE (1×2 mL) and MTH (1×2 mL) in an alternating fashion.

Alpha Sulfonamide Formation (R$_1$): The resin was slurried in THF (0.5 mL) and to this was added a 0.5M solution of the sulfonyl chloride in THF (1.0 mL) (see table 1) followed by a 1.0M solution of DiPEA in THF (0.5 mL). The reaction was agitated 20 h. and then filtered. The resin was washed with DCE (2×2 mL) followed by methanol (2×2 mL) and DCE (2×2 mL) in an alternating fasion.

Dde Deprotection: The resin was treated with 2% Hydrazine in DMF (1.5 mL). The resin was agitated for 25 minutes and then filtered. Following the final filtration, the resin was washed with DMF (2×2 mL). The resin was then washed twice each with DCE (1×2 mL) and MTH (1×2 mL) in an alternating fashion.

Beta Sulfonamide Formation (R$_2$): The resin was slurried in THF (0.5 mL) and to this was added a 0.5M solution of the sulfonyl chloride in THF (1.0 mL) (see table 1) followed by a 1.0M solution of DiPEA in THF (0.5 mL). The reaction was agitated 20 h. and then filtered. The resin was washed with DCE (2×2 mL) followed by methanol (2×2 mL) and DCE (2×2 mL) in an alternate fasion.

Hydroxylamine Cleavage: Hydroxylamine hydrochloride (9.2 g) was dissolved in methanol (50 mL) by heating. In a separate flask, potassium hydroxide (10.3 g) was dissolved in hot methanol (25 mL). Both solutions were allowed to cool to near room temperature before the KOH solution was slowly added to the hydroxylamine solution. The exothermic reaction produced a white precipitate which was removed by filtration. The filtrate was collected and stored in the ice box for 72 h. After 72 h., the filtrate was once again filtered, placed in an amber bottle and stored in the refrigerator.

The resin was slurried in THF (1.25 mL) and to this was added the cleavage cocktail (0.250 mL). The reaction was allowed to agitate for 72 h. at which time the resin was filtered and the filtrate was collected. The resin was washed once with methanol (0.5 mL) and this washing was added to the filtrate. To the filtrate was added 1N HCl solution (0.170 mL) and all volatiles were then removed by evaporation Example 15

The following compounds are prepared using method described above:

N-Hydroxy-2-[(4-methoxyphenylsulfonyl)amino]-3-[(4-methoxyphenylsulfonyl)amino]-propanamide MS (ESI): 460 (M+H$^+$).

N-Hydroxy-2-[(4-methoxyphenylsulfonyl)amino]-3-[(camphorsulfonyl)amino]-propanamide MS (ESI): 504 (M+H$^+$).

N-Hydroxy-2-[(4-methoxyphenylsulfonyl)amino]-3-[(1-naphthalenylsulfonyl)amino]-propanamide MS (ESI): 480 (M+H$^+$).

N-Hydroxy-2-[(4-methoxyphenylsulfonyl)amino]-3-[(2,4-difluorophenylsulfonyl)amino]-propanamide MS (ESI): 466 (M+H$^+$).

N-Hydroxy-2-[(4-methoxyphenylsulfonyl)amino]-3-[(2,4,6-trimethylphenylsulfonyl)amino]-propanamide MS (ESI): 472 (M+H$^+$).

N-Hydroxy-2-[(4-methoxyphenylsulfonyl)amino]-3-[(4-t-butylphenylsulfonyl)amino]-propanamide MS (ESI): 486 (M+H$^+$).

N-Hydroxy-2-[(4-methoxyphenylsulfonyl)amino]-3-[(2,5-dichlorophenylsulfonyl)amino]-propanamide MS (ESI): 499 (M+H$^+$).

N-Hydroxy-2-[(4-methoxyphenylsulfonyl)amino]-3-[(4-chlorophenylsulfonyl)amino]-propanamide MS (ESI): 464 (M+H$^+$).

N-Hydroxy-2-[(camphorsulfonyl)amino]-3-[(4-methoxyphenylsulfonyl)amino]-propanamide MS (ESI): 504 (M+H$^+$).

N-Hydroxy-2-[(camphorsulfonyl)amino]-3-[(camphorsulfonyl)amino]-propanamide MS (ESI): 548 (M+H$^+$).

N-Hydroxy-2-[(camphorsulfonyl)amino]-3-[(1-naphthalenylsulfonyl)amino]-propanamide MS (ESI): 524 (M+H$^+$).

N-Hydroxy-2-[(camphorsulfonyl)amino]-3-[(2,4-difluorophenylsulfonyl)amino]-propanamide MS (ESI): 510 (M+H$^+$).

N-Hydroxy-2-[(camphorsulfonyl)amino]-3-[(2,4,6-trimethylphenylsulfonyl)amino]-propanamide MS (ESI): 516 (M+H$^+$).

N-Hydroxy-2-[(camphorsulfonyl)amino]-3-[(4-t-butylphenylsulfonyl)amino]-propanamide MS (ESI): 530 (M+H$^+$).

N-Hydroxy-2-[(camphorsulfonyl)amino]-3-[(2,5-dichlorophenylsulfonyl)amino]-propanamide MS (ESI): 543 (M+H$^+$).

N-Hydroxy-2-[(camphorsulfonyl)amino]-3-[(4-chlorophenylsulfonyl)amino]-propanamide MS (ESI): 508 (M+H$^+$).

N-Hydroxy-2-[(1-naphthalenylsulfonyl)amino]-3-[(4-methoxyphenylsulfonyl)amino]-propanamide MS (ESI): 480 (M+H$^+$).

N-Hydroxy-2-[(1-naphthalenylsulfonyl)amino]-3-[(camphorsulfonyl)amino]-propanamide MS (ESI): 524 (M+H$^+$).

N-Hydroxy-2-[(1-naphthalenylsulfonyl)amino]-3-[(1-naphthalenylsulfonyl)amino]-propanamide MS (ESI): 500 (M+H$^+$).

N-Hydroxy-2-[(1-naphthalenylsulfonyl)amino]-3-[(2,4-difluorophenylsulfonyl)amino]-propanamide MS (ESI): 486 (M+H$^+$).

N-Hydroxy-2-[(1-naphthalenylsulfonyl)amino]-3-[(2,4,6-trimethylphenylsulfonyl)amino]-propanamide MS (ESI): 492 (M+H$^+$).

N-Hydroxy-2-[(1-naphthalenylsulfonyl)amino]-3-[(4-t-butylphenylsulfonyl)amino]-propanamide MS (ESI): 506 (M+H$^+$).

N-Hydroxy-2-[(1-naphthalenylsulfonyl)amino]-3-[(2,5-dichlorophenylsulfonyl)amino]-propanamide MS (ESI): 519 (M+H$^+$).

N-Hydroxy-2-[(1-naphthalenylsulfonyl)amino]-3-[(4-chlorophenylsulfonyl)amino]-propanamide MS (ESI): 484 (M+H$^+$).

N-Hydroxy-2-[(2,4-difluorophenylsulfonyl)amino]-3-[(4-methoxyphenylsulfonyl)amino]-propanamide MS (ESI): 466 (M+H$^+$).

N-Hydroxy-2-[(2,4-difluorophenylsulfonyl)amino]-3-[(camphorsulfonyl)amino]-propanamide MS (ESI): 510 (M+H$^+$).

N-Hydroxy-2-[(2,4-difluorophenylsulfonyl)amino]-3-[(1-naphthalenylsulfonyl)amino]-propanamide MS (ESI): 486 (M+H$^+$).

N-Hydroxy-2-[(2,4-difluorophenylsulfonyl)amino]-3-[(2,4-difluorophenylsulfonyl)amino]-propanamide MS (ESI): 472 (M+H$^+$).

N-Hydroxy-2-[(2,4-difluorophenylsulfonyl)amino]-3-[(2,4,6-trimethylphenylsulfonyl)amino]-propanamide MS (ESI): 478 (M+H$^+$).

N-Hydroxy-2-[(2,4-difluorophenylsulfonyl)amino]-3-[(4-t-butylphenylsulfonyl)amino]-propanamide MS (ESI): 492 (M+H$^+$).

N-Hydroxy-2-[(2,4-difluorophenylsulfonyl)amino]-3-[(2,5-dichlorophenylsulfonyl)amino]-propanamide MS (ESI): 505 (M+H$^+$).

N-Hydroxy-2-[(2,4-difluorophenylsulfonyl)amino]-3-[(4-chlorophenylsulfonyl)amino]-propanamide MS (ESI): 470 (M+H$^+$).

N-Hydroxy-2-[(2,4,6-trimethylphenylsulfonyl)amino]-3-[(4-methoxyphenylsulfonyl)amino]-propanamide MS (ESI): 472 (M+H$^+$).

N-Hydroxy-2-[(2,4,6-trimethylphenylsulfonyl)amino]-3-[(camphorsulfonyl)amino]-propanamide MS (ESI): 516 (M+H$^+$).

N-Hydroxy-2-[(2,4,6-trimethylphenylsulfonyl)amino]-3-[(1-naphthalenylsulfonyl)amino]-propanamide MS (ESI): 492 (M+H$^+$).

N-Hydroxy-2-[(2,4,6-trimethylphenylsulfonyl)amino]-3-[(2,4-difluorophenylsulfonyl)amino]-propanamide MS (ESI): 478 (M+H$^+$).

N-Hydroxy-2-[(2,4,6-trimethylphenylsulfonyl)amino]-3-[(2,4,6-trimethylphenylsulfonyl)amino]-propanamide MS (ESI): 484 (M+H$^+$).

N-Hydroxy-2-[(2,4,6-trimethylphenylsulfonyl)amino]-3-[(4-t-butylphenylsulfonyl)amino]-propanamide MS (ESI): 498 (M+H$^+$).

N-Hydroxy-2-[(2,4,6-trimethylphenylsulfonyl)amino]-3-[(2,5-dichlorophenylsulfonyl)amino]-propanamide MS (ESI): 511 (M+H$^+$).

N-Hydroxy-2-[(2,4,6-trimethylphenylsulfonyl)amino]-3-[(4-chlorophenylsulfonyl)amino]-propanamide MS (ESI): 476 (M+H$^+$).

N-Hydroxy-2-[(4-t-butylphenylsulfonyl)amino]-3-[(4-methoxyphenylsulfonyl)amino]-propanamide MS (ESI): 486 (M+H$^+$).

N-Hydroxy-2-[(4-t-butylphenylsulfonyl)amino]-3-[(camphorsulfonyl)amino]-propanamide MS (ESI): 530 (M+H$^+$).

N-Hydroxy-2-[(4-t-butylphenylsulfonyl)amino]-3-[(1-naphthalenylsulfonyl)amino]-propanamide MS (ESI): 506 (M+H$^+$).

N-Hydroxy-2-[(4-t-butylphenylsulfonyl)amino]-3-[(2,4-difluorophenylsulfonyl)amino]-propanamide MS (ESI): 492 (M+H$^+$).

N-Hydroxy-2-[(4-t-butylphenylsulfonyl)amino]-3-[(2,4,6-trimethylphenylsulfonyl)amino]-propanamide MS (ESI): 498 (M+H$^+$).

N-Hydroxy-2-[(4-t-butylphenylsulfonyl)amino]-3-[(4-t-butylphenylsulfonyl)amino]-propanamide MS (ESI): 512 (M+H$^+$).

N-Hydroxy-2-[(4-t-butylphenylsulfonyl)amino]-3-[(2,5-dichlorophenylsulfonyl)amino]-propanamide MS (ESI): 525 (M+H$^+$).

N-Hydroxy-2-[(4-t-butylphenylsulfonyl)amino]-3-[(4-chlorophenylsulfonyl)amino]-propanamide MS (ESI): 490 (M+H$^+$).

N-Hydroxy-2-[(2,5-dichlorophenylsulfonyl)amino]-3-[(4-methoxyphenylsulfonyl)amino]-propanamide MS (ESI): 499 (M+H$^+$).

N-Hydroxy-2-[(2,5-dichlorophenylsulfonyl)amino]-3-[(camphorsulfonyl)amino]-propanamide MS (ESI): 543 (M+H$^+$).

N-Hydroxy-2-[(2,5-dichlorophenylsulfonyl)amino]-3-[(1-naphthalenylsulfonyl)amino]-propanamide MS (ESI): 519 (M+H$^+$).

N-Hydroxy-2-[(2,5-dichlorophenylsulfonyl)amino]-3-[(2,4-difluorophenylsulfonyl)amino]-propanamide MS (ESI): 505 (M+H$^+$).

N-Hydroxy-2-[(2,5-dichlorophenylsulfonyl)amino]-3-[(2,4,6-trimethylphenylsulfonyl)amino]-propanamide MS (ESI): 511 (M+H$^+$).

N-Hydroxy-2-[(2,5-dichlorophenylsulfonyl)amino]-3-[(4-t-butylphenylsulfonyl)amino]-propanamide MS (ESI): 525 (M+H$^+$).

N-Hydroxy-2-[(2,5-dichlorophenylsulfonyl)amino]-3-[(2,5-dichlorophenylsulfonyl)amino]-propanamide MS (ESI): 538 (M+H$^+$).

N-Hydroxy-2-[(2,5-dichlorophenylsulfonyl)amino]-3-[(4-chlorophenylsulfonyl)amino]-propanamide MS (ESI): 503 (M+H$^+$).

N-Hydroxy-2-[(4-chlorophenylsulfonyl)amino]-3-[(4-methoxyphenylsulfonyl)amino]-propanamide MS (ESI): 464 (M+H$^+$).

N-Hydroxy-2-[(4-chlorophenylsulfonyl)amino]-3-[(camphorsulfonyl)amino]-propanamide MS (ESI): 508 (M+H$^+$).

N-Hydroxy-2-[(4-chlorophenylsulfonyl)amino]-3-[(1-naphthalenylsulfonyl)amino]-propanamide MS (ESI): 484 (M+H$^+$).

N-Hydroxy-2-[(4-chlorophenylsulfonyl)amino]-3-[(2,4-difluorophenylsulfonyl)amino]-propanamide MS (ESI): 470 (M+H$^+$).

N-Hydroxy-2-[(4-chlorophenylsulfonyl)amino]-3-[(2,4,6-trimethylphenylsulfonyl)amino]-propanamide MS (ESI): 476 (M+H$^+$).

N-Hydroxy-2-[(4-chlorophenylsulfonyl)amino]-3-[(4-t-butylphenylsulfonyl)amino]-propanamide MS (ESI): 490 (M+H$^+$).

N-Hydroxy-2-[(4-chlorophenylsulfonyl)amino]-3-[(2,5-dichlorophenylsulfonyl)amino]-propanamide MS (ESI): 503 (M+H$^+$).

N-Hydroxy-2-[(4-chlorophenylsulfonyl)amino]-3-[(4-chlorophenylsulfonyl)amino]-propanamide MS (ESI): 469 (M+H$^+$).

N-Hydroxy-2-[(4-methylphenylsulfonyl)amino]-3-[(4-methoxyphenylsulfonyl)amino]-propanamide MS (ESI): 444 (M+H$^+$).

N-Hydroxy-2-[(4-methylphenylsulfonyl)amino]-3-[(camphorsulfonyl)amino]-propanamide MS (ESI): 488 (M+H$^+$).

N-Hydroxy-2-[(4-methylphenylsulfonyl)amino]-3-[(1-naphthalenylsulfonyl)amino]-propanamide MS (ESI): 464 (M+H$^+$).

N-Hydroxy-2-[(4-methylphenylsulfonyl)amino]-3-[(2,4-difluorophenylsulfonyl)amino]-propanamide MS (ESI): 450 (M+H$^+$).

N-Hydroxy-2-[(4-methylphenylsulfonyl)amino]-3-[(2,4,6-trimethylphenylsulfonyl)amino]-propanamide MS (ESI): 456 (M+H$^+$).

N-Hydroxy-2-[(4-methylphenylsulfonyl)amino]-3-[(4-t-butylphenylsulfonyl)amino]-propanamide MS (ESI): 470 (M+H$^+$).

N-Hydroxy-2-[(4-methylphenylsulfonyl)amino]-3-[(2,5-dichlorophenylsulfonyl)amino]-propanamide MS (ESI): 483 (M+H$^+$).

N-Hydroxy-2-[(4-methylphenylsulfonyl)amino]-3-[(4-chlorophenylsulfonyl)amino]-propanamide MS (ESI): 448 (M+H$^+$).

N-Hydroxy-2-[(n-decylsulfonyl)amino]-3-[(4-methoxyphenylsulfonyl)amino]-propanamide MS (ESI): 522 (M+H$^+$).

N-Hydroxy-2-[(n-decylsulfonyl)amino]-3-[(camphorsulfonyl)amino]-propanamide MS (ESI): 566 (M+H$^+$).

N-Hydroxy-2-[(n-decylsulfonyl)amino]-3-[(1-naphthalenylsulfonyl)amino]-propanamide MS (ESI): 542 (M+H$^+$).

N-Hydroxy-2-[(n-decylsulfonyl)amino]-3-[(2,4-difluorophenylsulfonyl)amino]-propanamide MS (ESI): 528 (M+H$^+$).

N-Hydroxy-2-[(n-decylsulfonyl)amino]-3-[(2,4,6-trimethylphenylsulfonyl)amino]-propanamide MS (ESI): 534 (M+H$^+$).

N-Hydroxy-2-[(n-decylsulfonyl)amino]-3-[(4-t-butylphenylsulfonyl)amino]-propanamide MS (ESI): 548 (M+H$^+$).

N-Hydroxy-2-[(n-decylsulfonyl)amino]-3-[(2,5-dichlorophenylsulfonyl)amino]-propanamide MS (ESI): 561 (M+H$^+$).

Example 16

The following compounds are prepared using the methodology described herein and that of of U.S. patent application Ser. No. 60/024,675, and the methodology therein is hereby incorporated by reference. In the following compounds, A is PORAr, and R is hydroxy.

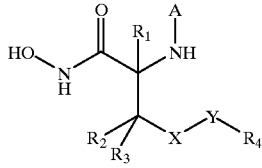
| | A | $R_1$ | $R_2$ | $R_3$ | X | Y | $R_4$ |
|---|---|---|---|---|---|---|---|
| 16A | $SO_2C_6H_4$-p-OMe | H | H | H | NH | CO | Me |
| 16B | $SO_2C_6H_4$-p-OPh | H | H | H | CO | NH | Ph |
| 16C | $SO_2C_6H_4$-p-$C_6H_4$-p-Br | H | —$CH_2CH_2CH_2CH_2$— | | S | — | i-Pr |
| 16D | $SO_2C_6H_4$-p-$C_6H_4$-p-Br | H | Me | Me | CO | NMe | 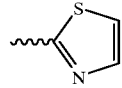 |
| 16E | $COC_6H_4$-p-OPh | H | Me | H | O | $CH_2$ | Ph |
| 16F | $SO_2C_6H_4$-p-OMe | H | H | H | — | — | 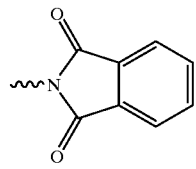 |
| 16G | POMePh | H | Me | Me | — | — | H |
| 16H | $POMe_2$ | Me | H | H | — | — | H |
| 16I | $SO_2C_6H_4$-p-OMe | H | H | H | — | — | 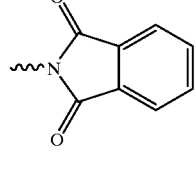 |
| 16J | $SO_2C_6H_4$-p-OMe | H | H | H | — | — | 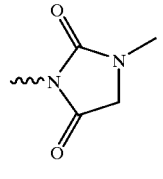 |
| 16K | $SO_2C_6H_4$-p-OMe | H | H | H | — | — | 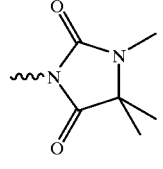 |
| 16L | $SO_2C_6H_4$-p-OMe | H | H | H | $CH_2$ | NHCO | 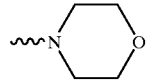 |
| 16M | $SO_2C_6H_4$-p-OPh | H | H | H | $CH_2$ | NHCO | 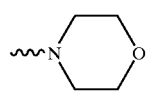 |
| 16N | $SO_2C_6H_4$-p-OMe | H | Me | Me | CO | — |  |
| 16O | $SO_2C_6H_4$-p-$OC_6H_4$-p-Cl | H | H | H | S | — | Me |

-continued

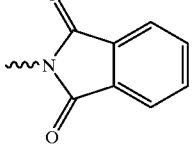

| | A | $R_1$ | $R_2$ | $R_3$ | X | Y | $R_4$ |
|---|---|---|---|---|---|---|---|
| 16P | $SO_2C_6H_4$-p-$OC_6H_4$-p-F | H | H | H | $SO_2$ | — | Me |
| 16Q | $SO_2C_6H_4$-p-$OC_6H_4$-p-Br | H | Me | Me | S | — | Me |
| 16R | $SO_2C_6H_4$-p-OMe | H | —$CH_2CH_2CH_2CH_2$— | | S | $CH_2$ | Ph |
| 16S | $SO_2C_6H_4$-p-$OC_6H_4$-p-Cl | H | —$CH_2CH_2CH_2CH_2CH_2$— | | S | $CH_2$ | $CH(CH_3)_2$ |
| 16T | $SO_2C_6H_4$-p-OMe | H | H | H | $CH_2$ | — | 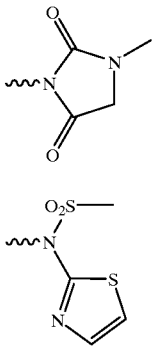 |
| 16U | $SO_2C_6H_4$-p-OMe | H | H | H | $CH_2$ | — | |
| 16V | $SO_2C_6H_4$-p-OMe | H | H | H | $CH_2$ | — | |

Methods

Example—is prepared by

Examples—are prepared by—in a manner analagous to example 1.

These examples provide the skilled artisan with sufficient guidance as to making the present invention and do not limit it in any way.

Composition and Method of Use Examples

The compounds of the invention are useful to prepare compositions for the treatment of ailments and the like. The following composition and method examples do not limit the invention, but provide guidance to the skilled artisan to prepare and use the compounds, compositions and methods of the invention. In each case the compounds formula I may be substituted for the example compound shown below with similar results.

The methods of use exemplified do not limit the invention, but provide guidance to the skilled artisan to use the compounds, compositions and methods of the invention. The skilled practitioner will appreciate that the examples provide guidance and may be varied based on condition and the patient.

Example A

A tablet composition for oral administration, according to the present invention, is made comprising:

| Component | Amount |
|---|---|
| Example 9 | 15. mg |
| Lactose | 120. mg |
| Maize Starch | 70. mg |
| Talc | 4. mg |
| Magnesium Stearate | 1. mg |

Other compounds having a structure according to Formula (I) are used with substantially similar results.

A human female subject weighing 60 kg (132 lbs), suffering from rheumatoid arthritis, is treated by a method of this invention. Specifically, for 2 years, a regimen of three tablets per day is administered orally to said subject.

At the end of the treatment period, the patient is examined and is found to have reduced inflammation, and improved mobility without concomitant pain.

Example B

A capsule for oral administration, according to the present invention, is made comprising:

| Component (% w/w) | Amount |
|---|---|
| Example 3 | 15% |
| Polyethylene glycol | 85% |

Other compounds having a structure according to Formula (I) are used with substantially similar results.

A human male subject weighing 90 kg (198 lbs), suffering from osteoarthritis, is treated by a method of this invention. Specifically, for 5 years, a capsule containing 70 mg of Example 3 is administered daily to said subject.

At the end of the treatment period, the patient is examined via orthoscopy, and found to have no further advancement of erosion/fibrillation of the articular cartilage.

Example C

A saline-based composition for local administration, according to the present invention, is made comprising:

| Component (% w/w) | Amount |
|---|---|
| Example 13 | 5% |
| Polyvinyl alcohol | 15% |
| Saline | 80% |

Other compounds having a structure according to Formula (I) are used with substantially similar results.

A patient having deep corneal abrasion applies the drop to each eye twice a day. Healing is speeded, with no visual sequelae.

Example D

An topical composition for local administration, according to the present invention, is made comprising:

| Component | Composition (% w/v) |
|---|---|
| Compound of Example 3 | 0.20 |
| Benzalkonium chloride | 0.02 |
| Thimerosal | 0.002 |
| d-Sorbitol | 5.00 |
| Glycine | 0.35 |
| Aromatics | 0.075 |
| Purified water | q.s. |
| Total = | 100.00 |
| Total = | 100.00 |

Any of the other compounds having a structure according to Formula (I) are used with substantially similar results.

A patient suffering from chemical burns applies the composition at each dressing change (b.i.d.). Scarring is substantially diminished.

Example E

A inhalation aerosol composition, according to the present invention, is made comprising:

| Component | Composition (% w/v) |
|---|---|
| Compound of Example 2 | 5.0 |
| Alcohol | 33.0 |
| Ascorbic acid | 0.1 |
| Menthol | 0.1 |
| Sodium Saccharin | 0.2 |
| Propellant (F12, F114) | q.s. |
| Total = | 100.0 |

Any of the other compounds having a structure according to Formula (I) are used with substantially similar results.

An asthma sufferer sprays 0.01 mL via a pump actuator into the mouth while inhaling. Asthma symptoms are diminished.

Example F

A topical opthalmic composition, according to the present invention, is made comprising:

| Component | Composition (% w/v) |
|---|---|
| Compound of Example 5 | 0.10 |
| Benzalkonium chloride | 0.01 |
| EDTA | 0.05 |
| Hydroxyethylcellulose (NATROSOL M ™) | 0.50 |
| Sodium metabisulfite | 0.10 |
| Sodium chloride (0.9%) | q.s. |
| Total = | 100.0 |

Any of the other compounds having a structure according to Formula (I) are used with substantially similar results.

A human male subject weighing 90 kg (198 lbs), suffering from corneal ulcerations, is treated by a method of this invention. Specifically, for 2 months, a saline solution containing 10 mg of Example 5 is administered to said subject's affected eye twice-daily.

Example G

A composition for parenteral administration is made comprising:

| Component | Amount |
|---|---|
| Example 4 | 100 mg/ml carrier |
| Carrier: | |
| sodium citrate buffer with (percent by weight of carrier): | |
| lecithin | 0.48% |
| carboxymethylcellulose | 0.53 |
| povidone | 0.50 |
| methyl paraben | 0.11 |
| propyl paraben | 0.011 |

The above ingredients are mixed, forming a suspension. Approximately 2.0 ml of the suspension is administered, via injection, to a human subject with a premetastatic tumor. The injection site juxtaposes the tumor. This dosage is repeated

Example H

A mouthwash composition is prepared;

| Component | % w/v |
|---|---|
| Example 1 | 3.00 |
| SDA 40 Alcohol | 8.00 |
| Flavor | 0.08 |
| Emulsifier | 0.08 |
| Sodium Fluoride | 0.05 |
| Glycerin | 10.00 |
| Sweetner | 0.02 |
| Benzoic acid | 0.05 |
| Sodium hydroxide | 0.20 |
| Dye | 0.04 |
| Water | balance to 100% |

A patient with gum disease uses 1 ml of the mouthwash thrice daily to prevent further oral degeneration.

Other compounds having a structure according to Formula I are used with substantially similar results.

Example I

A lozenge composition is prepared;

| Component | % w/v |
|---|---|
| Example 3 | 0.01 |
| Sorbitol | 17.50 |
| Mannitol | 17.50 |
| Starch | 13.60 |
| Sweetener | 1.20 |
| Flavor | 11.70 |
| Color | 0.10 |
| Corn Syrup | balance to 100% |

A patient uses the losenge to prevent loosening of an implant in the maxilla. Other compounds having a structure according to Formula I are used with substantially similar results.

Example J

Chewing Gum Composition

| Component | w/v % |
|---|---|
| Example 1 | 0.03 |
| Sorbitol crystals | 38.44 |
| Paloja-T gum base* | 20.00 |
| Sorbitol (70% aqueous solution) | 22.00 |
| Mannitol | 10.00 |
| Glycerine | 7.56 |
| Flavor | 1.00 |

A patient chews the gum to prevent loosening to prevent loosening of dentures.

Other compounds having a structure according to Formula I are used with substantially similar results.

Example K

| Components | w/v % |
|---|---|
| USP Water | 54.656 |
| Methylparaben | 0.05 |
| Propylparaben | 0.01 |
| Xanthan Gum | 0.12 |
| Guar Gum | 0.09 |
| Calcium carbonate | 12.38 |
| Antifoam | 1.27 |
| Sucrose | 15.0 |
| Sorbitol | 11.0 |
| Glycerin | 5.0 |
| Benzyl Alcohol | 0.2 |
| Citric Acid | 0.15 |
| Coolant | 0.00888 |
| Flavor | 0.0645 |
| Colorant | 0.0014 |

Example 1 is prepared by first mixing 80 kg of glycerin and all of the benzyl alcohol and heating to 65 C., then slowly adding and mixing together methylparaben, propylparaben, water, xanthan gum, and guar gum. Mix these ingredients for about 12 minutes with a Silverson in-line mixer. Then slowly add in the following ingredients in the following order: remaining glycerin, sorbitol, antifoam C, calcium carbonate, citric acid, and sucrose. Separately combine flavors and coolants and then slowly add to the other ingredients. Mix for about 40 minutes.

The patient takes the formulation to prevent flare up of colitis.

All references described herein are hereby incorporated by reference.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of this invention.

What is claimed is:

1. A compound having a structure according to Formula (I)

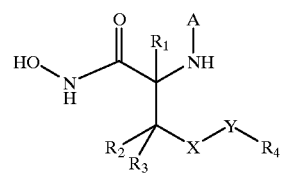

wherein

A is selected from SO$_2$Ar, COAr, CONHAr, and PORAr, where Ar is monocyclic or bicyclic aromatic or a monocyclic or bicyclic heteroaromatic, substituted or unsubstituted;

$R_1$ is alkyl or hydrogen;

$R_2$, $R_3$, and $R_4$ are each independently chosen from hydrogen, alkyl, aryl, heteroaryl, aryl-alkyl, alkoxy-alkyl, heterocycle, and heterocycle alkyl, and these substituents may be substituted or unsubstituted; rings can be formed by $R_2$ and $R_3$, $R_1$ and $R_2$ or $R_3$ and $R_4$;

X is a bond, a (C$_1$–C$_6$)alkyl, CO, or a heteroatom chosen from O, N, NZ, S, SO, or SO$_2$;

Y is a bond, a $(C_1-C_6)$alkyl, CO, $CO_2$, CONH, or a heteroatom chosen from O, N, NZ, S, SO, or $SO_2$; and Z is selected from hydrogen, $COR_4$, $COOR_4$, $CONHR_4$, $R_4$, $CSR_4$, $CSNHR_4$, and $SO_2R_4$;

or an optical isomer, diastereomer or enantiomer for Formula (I), or a pharmaceutically-acceptable salt, or biohydrolyzable amide, ester, or imide thereof.

2. The compound of claim 1, wherein A is $SO_2Ar$.

3. The compound of claim 1, wherein Ar is phenyl, substituted phenyl, or substituted biphenyl.

4. The compound of claim 3, wherein Ar is substituted phenyl or substituted biphenyl and the substitution is with hydroxy, alkoxy, phenoxy, nitro, halo, or phenyl.

5. The compound of claim 4, wherein Ar is substituted at the ortho or para position relative to the attachment of Ar to the molecule.

6. The compound of claim 1, wherein $R_1$ is H.

7. The compound of claim 1, wherein $R_2$ and $R_3$ can form a 3–9 membered ring containing from 0 to 4 heteroatoms, the heteroatoms can be chosen from O, N, NZ, S, SO, or $SO_2$, the ring can be substituted or unsubstituted.

8. The compound of claim 7, wherein the ring can be carbocyclic or heterocyclic in nature.

9. The compound of claim 8, wherein the ring may include tetrahydropyran, tetrahydrothiopyran, piperidino, or cyclohexyl.

10. The compound of claim 7, wherein the ring can be aryl or heteroaryl in nature, substituted or unsubstituted.

11. The compound of claim 1, wherein $R_2$ and $R_3$ are $CH_3$.

12. The compound of claim 1 wherein the X is NH or S.

13. The compound of claim 12 wherein $R_1$ is H, X is S, $R_2$ and $R_3$ are $CH_3$, Y is a bond, and $R_4$ is alkyl.

14. A pharmaceutical composition comprising:
    (a) a safe and effective amount of a compound of claim 1; and
    (b) a pharmaceutically-acceptable carrier.

15. A pharmaceutical composition comprising:
    (a) a safe and effective amount of a compound of claim 4; and
    (b) a pharmaceutically-acceptable carrier.

16. A pharmaceutical composition comprising:
    (a) a safe and effective amount of a compound of claim 5; and
    (b) a pharmaceutically-acceptable carrier.

17. A pharmaceutical composition comprising:
    (a) a safe and effective amount of a compound of claim 11; and
    (b) a pharmaceutically-acceptable carrier.

18. A pharmaceutical composition comprising:
    (a) a safe and effective amount of a compound of claim 12; and
    (b) a pharmaceutically-acceptable carrier.

19. A method for preventing or treating a disorder modulated by metalloproteases, wherein the disorder is chosen from the group consisting of arthritis; cancer, wherein the treatment prevents or arrests tumor growth and metastasis; cardiovascular disorders; skin disorders; ocular disorders; inflammation and gum disease by administering to a mammal in need of such treatment, a safe and effective amount of a metalloprotease inhibitor according to claim 1.

20. A method for preventing or treating a disorder according to claim 19, wherein the disorder is arthritis, and is chosen from the group comprising, osteoarthritis and rheumatoid arthritis.

21. A method for treating according to claim 19, wherein the disorder is cancer, and the treatment prevents or arrests tumor growth and metastasis.

22. A method for the preventing or treating a disorder according to claim 19, wherein the disorder is a cardiovascular disorder chosen from the group compromising dilated cardiomyopathy, congestive heart failure, atherosclerosis, plaque rupture, reperfusion injury, ischemia, chronic obstructive pulmonary disease, angioplasty restenosis and aortic aneurysm.

23. A method for the preventing or treating a disorder according to claim 19, wherein the disorder is an ocular disorder, and is chosen from the group comprising, corneal ulceration, lack of corneal healing, macular degeneration, and pterygium.

24. A method for preventing or treating a disorder according to claim 19, wherein the disorder is gum disease, and is chosen from the group comprising, periodontal disease, and gingivitis.

25. A method for preventing or treating a condition, according to claim 19, wherein the condition is skin condition chosen from the group comprising wrinkle repair and prevention, U. V. skin damage, epidermolysis bullosa, psoriasis, sclerodema, atopic dermatitis and scarring.

26. A method for preventing the loosening of prosthetic devices chosen from the group comprising joint replacements and dental prosthesis by administering to a mammal in need of such treatment, a safe and effective amount of a metalloprotease inhibitor according to claim 1.

27. A method for treating inflammatory conditions according to claim 19, chosen from the group comprising inflammatory bowel disease, Crohn's Disease, ulcerative colitis, pancreatitis, diverticulitis, acne inflammation, osteomylitis, bronchitis, arthritis, asthma.

28. A method of treating multiple sclerosis, comprising administering to a mammal in need of such treatment, a safe and effective amount of a metalloprotease inhibitor according to claim 1.

29. A method for treating musculoskeletal disease or cachexia comprising administering to a mammal in need of such treatment, a safe and effective amount of a metalloprotease inhibitor according to claim 1.

* * * * *